US010125105B2

United States Patent
Jewett et al.

(10) Patent No.: US 10,125,105 B2
(45) Date of Patent: *Nov. 13, 2018

(54) TRIAZABUTADIENES AS CLEAVABLE CROSS-LINKERS

(71) Applicant: ARIZONA BOARD OF REGENTS ON BEHALF OF THE UNIVERSITY OF ARIZONA, Tucson, AZ (US)

(72) Inventors: John C. Jewett, Tucson, AZ (US); Flora W. Kimani, Tucson, AZ (US); Lindsay Guzman, Tucson, AZ (US); Brandon M. Cornali, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/427,988

(22) Filed: Feb. 8, 2017

(65) Prior Publication Data

US 2017/0320834 A1 Nov. 9, 2017

Related U.S. Application Data

(63) Continuation-in-part of application No. 15/224,446, filed on Jul. 29, 2016, now Pat. No. 9,593,080, which (Continued)

(51) Int. Cl.
*C08G 59/00* (2006.01)
*C07D 233/88* (2006.01)
(Continued)

(52) U.S. Cl.
CPC .......... *C07D 233/88* (2013.01); *A61K 47/545* (2017.08); *C07D 403/12* (2013.01);
(Continued)

(58) Field of Classification Search
CPC ............ C08G 73/08; C08G 2261/3221; C08G 12/28; A61K 47/48; A61K 31/5575
See application file for complete search history.

(56) References Cited

U.S. PATENT DOCUMENTS 3,591,575 A 7/1971 Golda
3,607,542 A 9/1971 George et al.
(Continued)

FOREIGN PATENT DOCUMENTS

DE 265008 A1 2/1989
DE 4242428 A1 10/1993
(Continued)

OTHER PUBLICATIONS

Kimani and Jewett, 2015, Angewandte Chemie International Edition (DOI: 10.1002/anie.201411277—Online ahead of print).
(Continued)

*Primary Examiner* — Shane Fang
(74) *Attorney, Agent, or Firm* — Nguyen & Tarbet Law Firm

(57) ABSTRACT

Triazabutadiene molecules as cleavable cross-linkers adapted to cross-link components with click chemistry, e.g., clickable triazabutadienes. For example, in some embodiments, the triazabutadienes feature alkyne handles attached to the imidazole portion or the aryl portion of the triazabutadienes, wherein the alkyne handles can link to azide handles (e.g., azide handles disposed on other components) via click chemistry. Also described are methods of producing said clickable triazabutadienes and methods of use of said clickable triazabutadienes. The present invention also features methods of cleaving said clickable triazabutadienes, e.g., for liberating the diazonium species for further chemical reactions.

11 Claims, 15 Drawing Sheets

Related U.S. Application Data is a continuation-in-part of application No. 14/918,287, filed on Oct. 20, 2015, now Pat. No. 9,458,143, and a continuation-in-part of application No. PCT/US2015/035136, filed on Jun. 10, 2015, application No. 15/427,988, which is a continuation-in-part of application No. 15/317,894, filed as application No. PCT/US2015/035136 on Jun. 10, 2015, now Pat. No. 10,047,061.

(60) Provisional application No. 62/128,707, filed on Mar. 5, 2015, provisional application No. 62/114,735, filed on Feb. 11, 2015, provisional application No. 62/109,170, filed on Jan. 29, 2015, provisional application No. 62/010,861, filed on Jun. 11, 2014.

(51) Int. Cl.

| | |
|---|---|
| C09K 11/06 | (2006.01) |
| C07D 403/12 | (2006.01) |
| C07D 405/12 | (2006.01) |
| C07D 413/14 | (2006.01) |
| C07H 21/00 | (2006.01) |
| C09B 26/06 | (2006.01) |
| C09B 55/00 | (2006.01) |
| C09J 163/00 | (2006.01) |
| G01N 33/569 | (2006.01) |
| G01N 33/68 | (2006.01) |
| A61K 47/54 | (2017.01) |

(52) U.S. Cl.
CPC ......... *C07D 405/12* (2013.01); *C07D 413/14* (2013.01); *C07H 21/00* (2013.01); *C09B 26/06* (2013.01); *C09B 55/003* (2013.01); *C09J 163/00* (2013.01); *C09K 11/06* (2013.01); *G01N 33/56983* (2013.01); *G01N 33/6845* (2013.01); *C09K 2211/1048* (2013.01)

(56) References Cited

U.S. PATENT DOCUMENTS

| | | | |
|---|---|---|---|
| 3,959,210 | A | 5/1976 | Lipatova et al. |
| 4,107,353 | A | 8/1978 | Gabriel et al. |
| 4,218,279 | A | 8/1980 | Green |
| 4,356,050 | A | 10/1982 | Crivello et al. |
| 4,602,073 | A | 7/1986 | Skoultchi et al. |
| 5,856,373 | A | 1/1999 | Kaisaki et al. |
| 8,603,451 | B2 | 12/2013 | Zhang et al. |
| 8,617,827 | B2 | 12/2013 | Hell et al. |
| 9,458,143 | B1 | 10/2016 | Jewett et al. |
| 9,593,080 | B1 | 3/2017 | Jewett et al. |
| 2002/0197439 | A1 | 12/2002 | Berneth et al. |
| 2004/0241205 | A1 | 12/2004 | Babich et al. |
| 2005/0080260 | A1 | 4/2005 | Mills et al. |
| 2007/0049587 | A1 | 3/2007 | Zbinden et al. |
| 2007/0098807 | A1 | 5/2007 | Babich et al. |
| 2007/0104719 | A1 | 5/2007 | Carter et al. |
| 2009/0048222 | A1 | 2/2009 | Bell et al. |
| 2009/0286308 | A1 | 11/2009 | Berthelot et al. |
| 2011/0245287 | A1 | 10/2011 | Holaday et al. |
| 2017/0114033 | A1 | 4/2017 | Jewett et al. |

FOREIGN PATENT DOCUMENTS

| | | |
|---|---|---|
| WO | WO 2008/090554 A2 | 7/2008 |
| WO | WO 2009/137916 A1 | 11/2009 |
| WO | WO2015073746 A2 | 5/2015 |
| WO | WO 2015/191735 A1 | 12/2015 |

OTHER PUBLICATIONS

Zhong et al., 2014, Nature Nanotechnology 9, 858-866.
Stewart et al., 2011, J Polym Sci B Polym Phys 49(11):757-771.
Poulsen et al., 2014, Biofouling 30(4):513-23.
Stewart, 2011, Appl Microbial Biotechnol 89(1):27-33.
Stewart et al.,, 2011, Adv Colloid Interface Sci 167(1-2):85-93.
Hennebert et al., 2015, Interface Focus 5(1):2014.
Y. Modis, S. Ogata, D. Clements, S. C. Harrison, Nature 2004, 427, 313-319.
C. D. Blanchette, Y. H. Woo, C. Thomas, N. Shen, T. A Sulchek, A. L. Hiddessen, PLoS One 2009, 4, e6056.
J. Han, K. Burgess, Chem. Rev. 2010, 110, 2709-2728.
J. Kalia, R. T. Raines, Angew. Chem. Int. Ed. Engl. 2008, 47, 7523-7526.
J. Kalia, R. T. Raines, Angew. Chem. 2008, 120, 7633-7636.
J. Z. Du, X. J. Du, C. Q. Mao, J. Wang, J. Am. Chem. Soc. 2011, 133, 17560-17563.
E. H. Cordes, H. G. Bull, Chem. Rev. 1974, 74, 581-603.
A. Luong, T. Issarapanichkit, S. D. Kong, R. Fonga, J. Yang, Org. Biomol. Chem. 2010, 8, 5105-5109.
Fanghänel, R. Hänsel, W. Ortmann, J. Hohlfeld, J. Prakt. Chem. 1975, 317, 631-640.
H.-T. Dorsch, H. Hoffmann, R. Hansel, G. Rasch, E. Fanghänel, J. Prakt. Chem. 1976, 318, 671-680.
E. Fanghänel, R. Hänsel, J. Hohlfeld, J. Prakt. Chem. 1977, 319, 485-493.
E. Fanghänel, H. Poleschner, R. Radeglia, R. Hänsel, J. Prakt. Chem. 1977, 319, 813-826.
E. Fanghänel, J. Hohlfeld, J. Prakt. Chem. 1981, 323, 253-261.
R. Radeglia, R. Wolff, T. Steiger, S. Simova, E. Fanghanel, J. Prakt. Chem. 1984, 5, 511-514.
E. Fanghänel, W. Ortmann, A. Hennig, J. Prakt. Chem. 1988, 330, 27-34.
E. Fanghänel, W. Ortmann, J. Prakt. Chem. 1989, 331, 721-725.
E. Fanghänel, J. U. Bauroth, H. Hentschel, E Gußmann, H. Alzyadi, W. Ortmann, J. Prakt.Chem. 1992, 334, 241-247.
D. M. Khramov, C. W. Bielawski, Chem. Commun. 2005, 4958-4960.
S. Dahmen, S. Brase, Org. Lett 2000, 2, 3563-3565.
S. Brase, Acc. Chem. Res. 2004, 37, 805-816.
D. Jishkariani, C. D. Hall, A. Demircan, B. J. Tomlin, P. J. Steel, A. R. Katritzky, J. Org. Chem. 2013, 78, 3349-3354.
D. M. Khramov, C. W. Bielawski, J. Org. Chem. 2007, 72, 9407-9417.
A. G. Tennyson, E. J. Moorhead, B. L. Madison, J. A. V. ER, V. M. Lynch, C. W. Bielawski, Eur. J. Org. Chem. 2010, 6277-6282.
W. Herrmann, C. Köcher, Angew. Chem. Int. Ed. 1997, 36, 2162-2187.
W. Herrmann, C. Köcher, Angew. Chem. 1997, 109, 2256-2282.
N. Marion, S. Díez-González, S. P. Nolan, Angew. Chem. Int. Ed. Engl. 2007, 46, 2988-3000.
N. Marion, S. Díez-González, S. P. Nolan, Angew. Chem. 2007, 119, 3046-3058.
A. F. Hegarty, In the Chemistry of Diazonium and Diazo Groups, vol. 2 (Ed.: S. Patai), John Wiley & Sons, Ltd., New York, NY, 1978, pp. 511-591.
L. P. Hammett, J. Am. Chem. Soc. 1937, 59, 96-103.
B. M. Tracey, D. E. G. Shuker, Chem. Res. Toxicol. 1997, 10, 1378-1386.
J. M. Hooker, E. W. Kovacs, M. B. Francis, J. Am. Chem. Soc. 2004, 126, 3718-3719.
J. Gavrilyuk, H. Ban, M. Nagano, W. Hakamata, C. F. Barbasiii, Bioconjugate Chem. 2012, 23, 2321-2328.
L. Wang, V. Gruzdys, N. Pang, F. Meng, X.-L. Sun, RSC Adv. 2014, 4, 39446.
European Journal of Inorganic Chemistry vol. 2013, Issue 12, p. 2020-2030, Apr. 2013 Elena García-Moreno, Elena Cerrada, M. José Bolsa, Asunción Luquin and Mariano Laguna.
European Journal of Medicinal Chemistry vol. 46, Issue 7, Jul. 2012, p. 2748-2758, Marijana Hranjeca, Borka Lučića, Ivana Ratkajb, Sandra Kraljević Pavelićb, Ivo Piantanidac, Krešimir Pavelićb, Grace Karminski-Zamola.

(56) References Cited

OTHER PUBLICATIONS

Flora Kimani and John Jewett, DOI: 10.1002/anie.201411277 Water-Soluble Triazabutadienes that Release Diazonium Species upon Protonation under Physiologically Relevant Conditions.
Chao Zhong, Thomas Gurry, Allen A. Cheng, Jordan Downey, Zhengtao Deng, Collin M. Stultz, Timothy K. Lu, Nature Nanotechnology 9, 858-866 (2014).
Stewart RJ, Ransom TC, Hlady V, J Polym Sci B Polym Phys. Jun. 2011;49(11):757-771.
Poulsen N, Kröger N, Harrington MJ, Brunner E, Paasch S, Buhmann MT, Biofouling. 2014;30(4):513-23.
Stewart RJ, Appl Microbial Biatechnol. Jan. 2011;89(1):27-33.
Stewart RJ, Wang CS, Shao H, Adv Colloid Interface Sci. Sep. 14, 2011;167(1-2):85-93.
Hennebert E, Maldonado B, Ladurner P, Flammang P, Santos R, Interface Focus. Feb. 6, 2015;5(1):2014.
Phosphate-buffered saline (PBS) CSH Protocols. "http://cshprotocols.cshlp.org/content/2006/1/pdb.rec8247".
Cornaii, 'Development of Clickable Triazabutadienes as Cleavable Cross-linkers', a thesis submitted to the Faculty of the Department of Chemistry and Biochemistry in Partial Fulfillment of the Requirements for the Degree of Master of Science, the University of Arizona, Apr. 8, 2016.

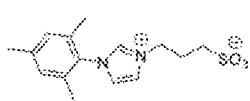
FIG. 6A
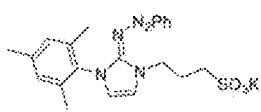
FIG. 6B
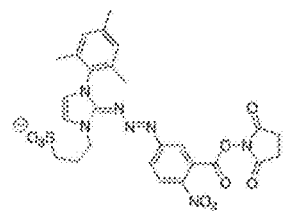
FIG. 6C
FIG. 6D
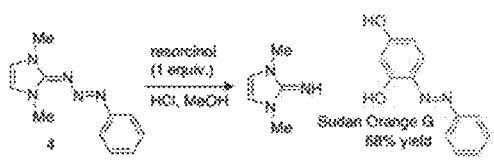
FIG. 6E
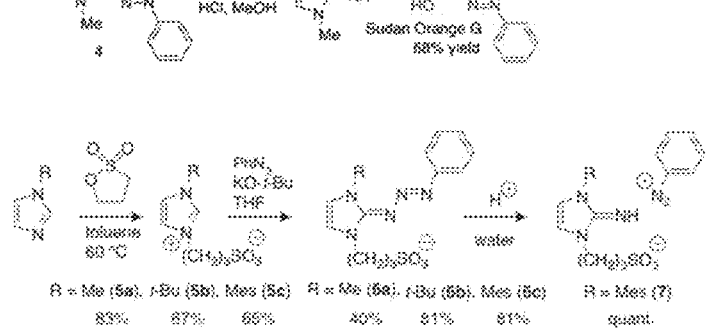
FIG. 6F
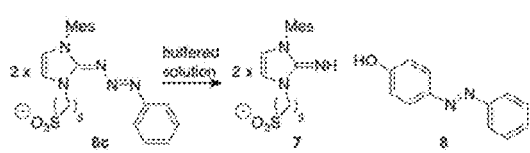
FIG. 6G
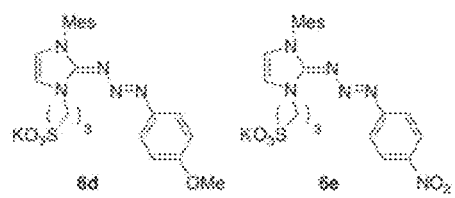
FIG. 6H
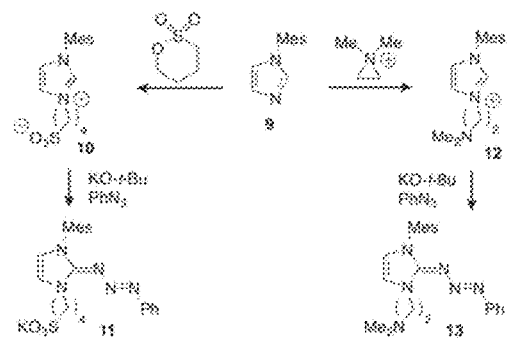

Formula A

Formula B

Formula C 6 (TBD-6)

7 (TBD-7)

TRIAZABUTADIENES AS CLEAVABLE CROSS-LINKERS

CROSS REFERENCE

This application is a continuation in part of U.S. patent application Ser. No. 15/224,446 filed Jul. 29, 2016, which is a continuation in part of U.S. patent application Ser. No. 14/918,287 filed Oct. 20, 2015, now U.S. Pat. No. 9,458,143, which is a continuation in part of PCT/US15/35136 filed on Jun. 10, 2015, which claims priority to U.S. Provisional Application No. 62/010,861, filed Jun. 11, 2014, U.S. Provisional Application No. 62/109,170 filed Jan. 29, 2015, U.S. Provisional Application No. 62/114,735 filed Feb. 11, 2015, and U.S. Provisional Application No. 62/128,707 filed Mar. 5, 2015, the specifications of which are incorporated herein in their entirety by reference.

This application is a continuation in part of U.S. patent application Ser. No. 15/317,894 filed Dec. 9, 2016, which is a 371 application of PCT/US15/35136 filed on Jun. 10, 2015, which claims priority to U.S. Provisional Application No. 62/010,861 filed Jun. 11, 2014, U.S. Provisional Application No. 62/109,170 filed Jan. 29, 2015, U.S. Provisional Application No. 62/114,735 filed Feb. 11, 2015, and U.S. Provisional Application No. 62/128,707 filed Mar. 5, 2015, the specifications of which are incorporated herein in their entirety by reference.

BACKGROUND OF THE INVENTION

Triazabutadienes can be triggered to release a highly reactive diazonium species in a pH-dependent way when placed in acidic conditions. Electron-rich phenyl systems such as resorcinol or tyrosine residues can react with the diazonium compounds to form stable azobenzene products. Alterations of these triazabutadiene motifs allow for modification of functionality, solubility, and other molecular properties. For example, triazabutadienes can be modified to function as cross-linkers; cleavage of the cross-linker triazabutadiene can liberate the diazonium species, in some cases near a site of interest.

The present invention features triazabutadienes as cleavable cross-linkers, wherein the triazabutadienes allow for cross-linking with a secondary component via click chemistry (copper (I) catalyzed azide alkyne cycloaddition), e.g., "clickable" triazabutadienes. In some embodiments, the clickable triazabutadienes comprise or are linked to a first component (e.g., a protein, a drug, a surface, etc.) and via click chemistry said first component can be cross-linked to a second component (e.g., another protein, surface, etc.).

The present invention also features methods of producing said clickable triazabutadienes and methods of use of said clickable triazabutadienes. For example, the compositions of the present invention may be used as biological cross-linkers and methods of the present invention may be used for biological methods such as detecting protein-protein interactions, mapping drug-target interactions, discovering or characterizing host-pathogen interactions, etc. The present invention also features methods of cleaving said triazabutadienes, e.g., cleaving the clickable triazabutadienes that has undergone click chemistry and is in the cross-linking state. In some embodiments, cleavage of the cross-linking triazabutadiene liberates the diazonium species; thus, the present invention also features methods that feature diazonium reactions following cleavage of said linking triazabutadienes.

SUMMARY

The present invention features clickable triazabutadiene according to (a) Formula B (see FIG. 11A) wherein $X^1$ comprises a terminal alkyne handle; or (b) Formula C (see FIG. 11A) wherein either $X^1$ comprises a terminal alkyne, $X^2$ comprises a terminal alkyne handle, or both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; wherein the alkyne handles are adapted to cross-link to an azide handle of a linking component via click chemistry. In some embodiments, the triazabutadiene comprises is linked to a peptide, an oligonucleotide, or a drug. In some embodiments, the linking component with the azide handle comprises a peptide, an oligonucleotide, or a drug.

The present invention also feature a method of detecting an interaction between a first component and a second component, said method comprising cleaving a triazabutadiene linked to the first component via a first triazole formed from click chemistry and to the second component via a second triazole formed from click chemistry, wherein cleaving the triazabutadiene liberates a diazonium species whereupon the diazonium species reacts with an electron-rich phenyl system to form a detectable signal, said detectable signal being indicative of interaction between the first component and the second component. In some embodiments, the triazabutadiene is according to Formula C, wherein both $X^1$ and $X^2$ comprised a terminal alkyne handle prior to formation of the first triazole and second triazole via click chemistry.

The present invention also features a method of linking a functional group or component to a clickable triazabutadiene, said functional group or component comprising an azide handle, said clickable triazabutadiene being according to (a) Formula B (see FIG. 11A) wherein $X^1$ comprises a terminal alkyne handle; or (b) Formula C (see FIG. 11) wherein either $X^1$ comprises a terminal alkyne, $X^2$ comprises a terminal alkyne handle, or both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; said method comprising subjecting the clickable triazabutadiene and functional group or component to copper click chemistry, wherein copper click chemistry links the clickable triazabutadiene and functional group or component via formation of a triazole from the alkyne handle and the azide handle. In some embodiments, the functional group comprises a water solubility functional group. In some embodiments, the component comprises a peptide, an oligonucleotide, or a drug.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 6A-FIG. 6H show non-limiting examples of triazabutadienes or reaction schemes involving triazabutadienes.

DETAILED DESCRIPTION OF THE INVENTION

I. Triazabutadiene Molecules

Figure 1:
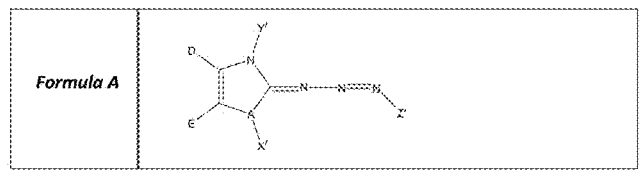
FIG. 1 shows non-limiting examples of triazabutadiene molecules.

The present invention features triazabutadiene molecules. Non-limiting examples of formulas for triazabutadiene molecules of the present invention are of shown in FIG. 1. For example, in some embodiments, triazabutadienes are according to Formula A. Examples of Formula A are shown as Formula I, II, III, and IV. The present invention is not limited to Formula A, Formula I, Formula II, Formula III, and Formula IV. Referring to FIG. 1, in some embodiments, A=S, O, or N. In some embodiments, D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl.

In some embodiments, $X^1$ is a moiety conferring water solubility. In some embodiments, $Y^1$ is a tri-substituted aryl group. In some embodiments, the $Y^1$ (e.g., the tri-substituted aryl group) comprises a NHS-ester moiety (e.g., for protein linkage); an oligonucleotide; a peptide; a fluorescence quencher; a pro-fluorophore; an alkyne (e.g., for click chemistry); a triazene (e.g., from click reaction); the like, or a combination thereof. In some embodiments, $Y^1$ comprises an aldehyde; an amine (e.g., Fmoc protected), aminooxy, halogen (e.g., radio isotope); the like, or a combination thereof. In some embodiments, $Z^1$ is an optionally substituted aryl. In some embodiments, $Z^1$ comprises a NHS-ester moiety; an oligonucleotide; a peptide; a fluorescence quencher; a pro-fluorophore; a biologically active acid labile compound; a prodrug comprising a phenolic functional group; releasable cargo; an alkyne (e.g., for click chemistry); a triazene (e.g., from click reaction); a polymerization residue (e.g., epoxide, polystyrene, alpha-beta-unsaturated ester acrylate, polyacrylamide, an amine, etc.), the like, or a combination thereof. In some embodiments, $Z^1$ comprises an aldehyde; an amine (e.g., Fmoc protected), aminooxy, halogen (e.g., radio isotope); the like, or a combination thereof.

In some embodiments, $X^1$ may comprise a functional group that confers water solubility. In some embodiments, $X^1$ comprise a moiety of the formula —$R^1$-$Q^1$, wherein $R^1$ is $C_{1-6}$ alkylene, and $Q^1$ is sulfate, sulfonate, phosphate, a quaternary ammonium cation, or an alkyl, aryl or propargylic containing moiety that can facilitate coupling to other azides via [3+2] cycloaddition chemistry. In some embodiments, $X^1$ is a moiety of the formula —$R^1$-$Q^1$, wherein $R^1$ is an alkane, e.g., $C_{1-6}$ alkylene. In some embodiments, $Q^1$ is sulfate (e.g., —(O)$_n$SO$_3$R$^a$, where n is 0 or 1, and R$^a$ is $C_{1-6}$ alkyl or typically H), phosphate (e.g., —(O)$_n$PO$_3$R$^a$, where n is 0 or 1, and R$^a$ is $C_{1-6}$ alkyl or typically H), or a quaternary ammonium cation (e.g., —[NR$^a$R$^b$R$^c$]$^+$, where each of R$^a$, R$^b$, and R$^c$ is independently H or $C_{1-6}$ alkyl). As used herein, the term "alkyl" refers to a saturated linear monovalent hydrocarbon moiety of one to twelve, typically one to six, carbon atoms or a saturated branched monovalent hydrocarbon moiety of three to twelve, typically three to six, carbon atoms. Examples of alkyl groups include, but are not limited to, methyl, ethyl, n-propyl, 2-propyl, tert-butyl, pentyl, and the like. The term "alkylene" refers to a saturated linear divalent hydrocarbon moiety of one to twelve, typically one to six, carbon atoms or a branched saturated divalent hydrocarbon moiety of three to twelve, typically three to six, carbon atoms. Examples of alkylene groups include, but are not limited to, methylene, ethylene, propylene, butylene, pentylene, and the like.

Triazabutadiene molecules of the present invention are readily soluble in water. In some embodiments, the solubility of the triazabutadiene molecules in water is at least 23 g/L of water (50 mM). In some embodiments, the triazabutadiene molecules are stable in pH 7.4 phosphate buffer. The phosphate buffer solutions are commercially available or can be prepared, for example, as described in http://cshprotocols.cshlp.org/content/2006/1/pdb.rec8247. In some instances, the half-life of the triazabutadiene molecules of the present invention in pH 7.4 phosphate buffer solution is at least 24 hours.

Stability of the triazabutadiene molecule can be measured in various ways. In some embodiments, stability is measured by the half-life of the molecule (or the half-life of the molecule in a particular buffer at a particular pH). In some embodiments, the molecule has a half-life of at least 12 hours in a pH 7.4 buffer. In some embodiments, the molecule has half-life of at least 24 hours in a pH 7.4 buffer. In some embodiments, the molecule has half-life of at least 36 hours in a pH 7.4 buffer. In some embodiments, the triazabutadiene molecule has a half-life of at least 8 hours. In some embodiments, the triazabutadiene molecule has a half-life of at least 10 hours. In some embodiments, the triazabutadiene molecule has a half-life of at least 12 hours. In some embodiments, the triazabutadiene molecule has a half-life of at least 20 hours. In some embodiments, the triazabutadiene molecule has a half-life of at least 24 hours. In some embodiments, the triazabutadiene molecule has a half-life of at least 30 hours. In some embodiments, the triazabutadiene molecule has a half-life of at least 36 hours. The present invention is not limited to the aforementioned examples of stability measurements.

Without wishing to limit the present invention to any theory or mechanism, it is believed that the triazabutadiene molecules of the present invention are advantageous because the triazabutadiene molecules can be easily modified (e.g., various different functional groups can be easily used as $X^1$, $Y^1$, or $Z^1$ (see FIG. 1). And, the release of the diazonium species following triazabutadiene molecule breakdown (via certain mechanisms, as described below) provides a functional group that can be taken advantage of in various applications. Also, it may be considered advantageous that the breakdown of the triazabutadiene molecule is irreversible.

II. Cleavage of Triazabutadiene Molecules a. Water and/or Low pH

Figure 2A:
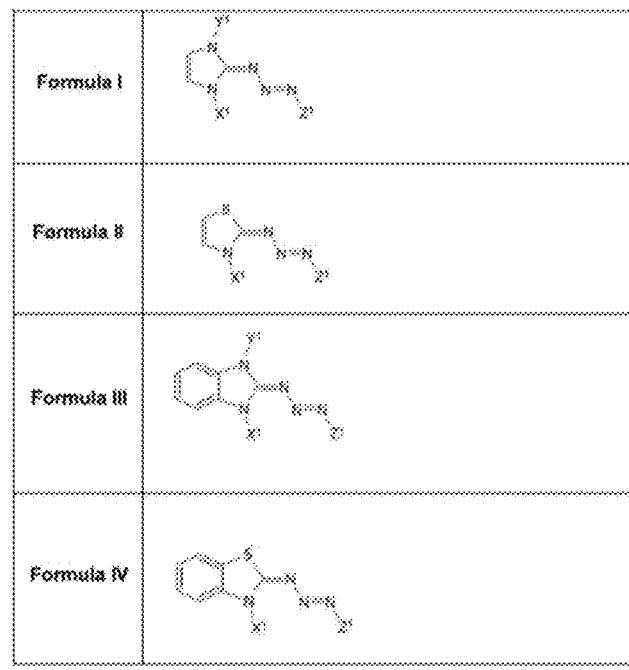
FIG. 2A shows triazabutadiene molecules undergoing decomposition to diazonium salts (and cyclic guanidine species). Note the reaction/equilibrium arrows are not to scale.
Figure 2A:
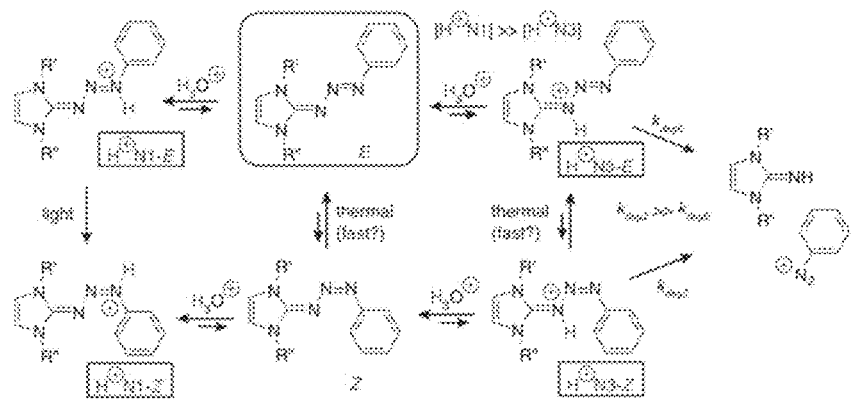

The present invention shows that triazabutadiene molecules may break down in the presence of water to generate reactive aryl diazonium compounds. For example, FIG. 2A shows that triazabutadiene molecules of the present invention can undergo decomposition to diazonium salts (reactive aryl diazonium compounds) and cyclic guanidine species. Aryl diazonium compounds can react with electron-rich aryl rings (e.g., aryl species wherein the bond of interest is a nitrogen-carbon bond; indoles, anilines, phenol-containing compounds such as resorcinol or tyrosine, etc.) to form stable azobenzene linkages (e.g., an aryl azo dye, e.g., Sudan Orange). (Note the present invention is not limited to the aforementioned phenol-containing species. In some embodiments, imidazole compounds (e.g., purine bases like guanine) may be used in lieu of a phenol-containing compound.) The diazonium species may not necessarily react with an electron-rich aryl rings compound (e.g., phenol species), for example if a phenol species is not present. The diazonium species may irreversibly extrude nitrogen gas to generate an aryl cation, which will rapidly be quenched by solvating water, thus synthesizing a new phenolic compound (e.g., HO-Ph, wherein Ph refers to the phenyl ring); thus, the diazonium portion of the triazabutadiene molecule may function as a masked hydroxyl group.

Figure 2B:
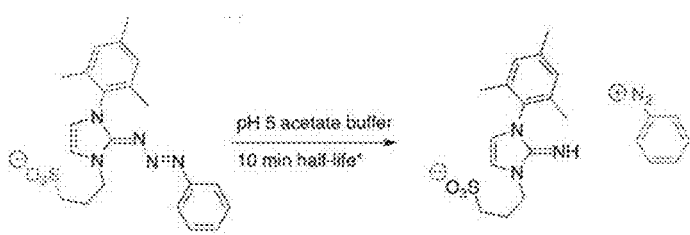
FIG. 2B shows a triazabutadiene molecule breaking down (in low pH conditions) to a diazonium species and a cyclic guanidine species.

In some embodiments, the triazabutadiene molecules are acid labile, e.g., unstable at particular pH levels (see FIG. 2B). For example, decreases in pH increase the rate at which the triazabutadiene molecules break down (the half life of the molecule decreases). In some embodiments, the triazabutadiene molecules are unstable at low (lowered) pH levels (e.g., lowered pH as compared to a particular pH that the molecule may be stored at, e.g., a pH wherein the molecule has a particular desired half life). Low pH levels, in some example, may be a sub-physiological pH (7.4 or less). In some embodiments, the triazabutadiene molecules are (more) unstable at pH 7.0 or less, pH 6.8 or less, pH 6.5 or less, pH 6.2 or less, pH 6.0 or less, pH 5.8 or less, pH 5.6 or less, pH 5.5 or less, pH 5.2 or less, pH 5.0 or less, etc.

The term 'low pH" may refer to several different pH levels. Since the functional groups attached to the molecule (e.g., see $X^1$, $Y^1$, $Z^1$ of Formula I) affect the stability of the molecule (as well as water solubility), the pH that is necessary to increase the rate of breakdown of the triazabutadiene molecule (e.g., the "lowered pH") may be different for different molecules. In some embodiments, the low pH is a pH of 7.4 or less. In some embodiments, the low pH is a pH of 7.2 or less. In some embodiments, the low pH is a pH of 7.0 or less. In some embodiments, the low pH is a pH of 6.8 or less. In some embodiments, the low pH is a pH of 6.6 or less. In some embodiments, the low pH is a pH of 6.6 or less. In some embodiments, the low pH is a pH of 6.6 or less. In some embodiments, the low pH is a pH of 6.5 or less. In some embodiments, the low pH is a pH of 6.4 or less. In some embodiments, the low pH is a pH of 6.2 or less. In some embodiments, the low pH is a pH of 6.0 or less. In some embodiments, the low pH is a pH of 5.8 or less. In some embodiments, the low pH is a pH of 5.5 or less. In some embodiments, the low pH is a pH of 5.0 or less.

In some embodiments, the triazabutadiene molecules can break down without the presence of the low pH (the molecules have half lives); however, in some embodiments, a lowered pH enhances the reaction (e.g., increases the rate of reaction). As such, a low pH may or may not be used with the molecules and/or methods of the present invention. In some embodiments, the triazabutadiene molecule has a half-life of no more than 1 hour in a pH 7.4 aqueous solution. In some embodiments, the triazabutadiene molecule has a half-life of no more than 30 minutes in a pH 7.4 aqueous solution. In some embodiments, the triazabutadiene molecule has a half-life of no more than 15 minutes in a pH 7.4 aqueous solution.

The present invention also features methods of breaking down triazabutadiene molecules. In some embodiments, the method comprises subjecting the molecule to water. In some embodiments, the method comprises subjecting the molecule to a low pH (e.g., a low pH that is appropriate for the molecule, e.g., a lowered pH that increases the rate at which the triazabutadiene molecule breaks down).

In some embodiments, the reaction of the triazabutadiene molecule to the diazonium species occurs in water within 10 seconds minutes. In some embodiments, the reaction of the triazabutadiene molecule to the diazonium species occurs in water within 30 seconds minutes. In some embodiments, the reaction of the triazabutadiene molecule to the diazonium species occurs in water within 1 minute. In some embodiments, the reaction of the triazabutadiene molecule to the diazonium species occurs in water within 5 minutes. In some embodiments, the reaction of the triazabutadiene molecule to the diazonium species occurs in water within 10 minutes. In some embodiments, the reaction of the triazabutadiene molecule to the diazonium species occurs in water within 15 minutes. In some embodiments, the reaction of the triazabutadiene molecule to the diazonium species occurs in water within 20 minutes. In some embodiments, the reaction of the triazabutadiene molecule to the diazonium species occurs in water within 25 minutes. In some embodiments, the reaction of the triazabutadiene molecule to the diazonium species occurs in water within 30 minutes. In some embodiments, the reaction of the triazabutadiene molecule to the diazonium species occurs in water within 45 minutes. In some embodiments, the reaction of the triazabutadiene molecule to the diazonium species occurs in water within 60 minutes.

In some embodiments, the diazonium species may be visually differentiated from the triazabutadiene species, e.g., the diazonium species is visually distinct (e.g., a different color) from the triazabutadiene molecule. If applicable, in some embodiments, the aryl azo dye may be visually differentiated from the triazabutadiene species and the diazonium species, e.g., the aryl azo dye is visually distinct (e.g., a different color) from the triazabutadiene species and the diazonium species.

Given the possibility that the aryl azo dye is visually distinct from the triazabutadiene molecule (and/or the diazonium species), the present invention also features methods of producing a visually detectable molecule. In some embodiments, the method comprises providing a triazabutadiene molecule according to the present invention and subjecting the triazabutadiene molecule to water and/or a low pH (or light as discussed below, or light and low pH, etc.). The low pH (or light, or light and low pH, etc.) initiates (e.g., increases the rate of) the irreversible reaction to produce the diazonium species and the cyclic guanidine species. As previously discussed, the diazonium species may be visually distinct from the triazabutadiene molecule; therefore the reaction produces a visually detectable molecule.

b. Reductive Cleavage

Figure 3:
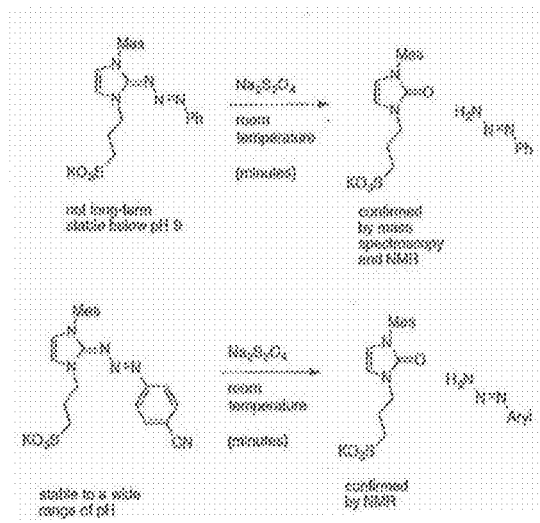
FIG. 3 shows reductive cleavage of triazabutadiene molecules.

Other mechanisms may be used to break down triazabutadiene molecules of the present invention. For example, in some embodiments, reducing conditions increase the rate at which the triazabutadiene molecules break down. Thus, the present invention also features methods of reductive cleavage of triazabutadiene molecules. For example, triazabutadiene molecules (e.g., triazabutadiene scaffolds) may be readily cleaved using reducing agents such as but not limited to sodium dithionite (sodium hydrosulfite) ($Na_2S_2O_4$) (see FIG. 3). In some embodiments, the reducing agent comprises lithium aluminum hydride, sodium borohydride, or the like.

In some embodiments, electrochemical reduction may be used in accordance with the present invention. Reductive cleavage of the triazabutadiene molecules provides a urea functionality and a terminal aryl triazene (see FIG. 3). In some embodiments, the aryl triazene is further reduced in the presence of excess reducing agent (e.g., sodium dithionite). In some embodiments, the reduction can be observed visually by the change in color of a solution. For example, there may be a subtle change of yellows that results from a loss of a shoulder in UV/vis spectrum.

In some embodiments, the ratio of the concentration of the triazabutadiene to the reducing agent is about 1:1. In some embodiments, the ratio of the concentration of the triazabutadiene to the reducing agent is about 1:2. The present invention is not limited to the aforementioned ratios. For example, in some embodiments, the ratio of the concentration of the triazabutadiene to the reducing agent is about 2:3, 4:5, etc. The present invention is not limited to the aforementioned ratio of concentrations.

In some embodiments, the reduction can occur within about 10 minutes, within about 15 minutes, within about 20 minutes, within about 25 min, within about 30 min, etc., at room temperature. Without wishing to limit the present invention to any theory or mechanism, it is believed that reductive cleavage of the triazabutadiene molecules is advantageous because it can occur rapidly (e.g., within 10 minutes, within 15 minutes). Also, the triazabutadiene molecules that are highly stable in acid (e.g., a p-CN derived triazabutadiene) may still be susceptible to reducing conditions.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

c. Light-Initiated Cleavage

Figure 4A:
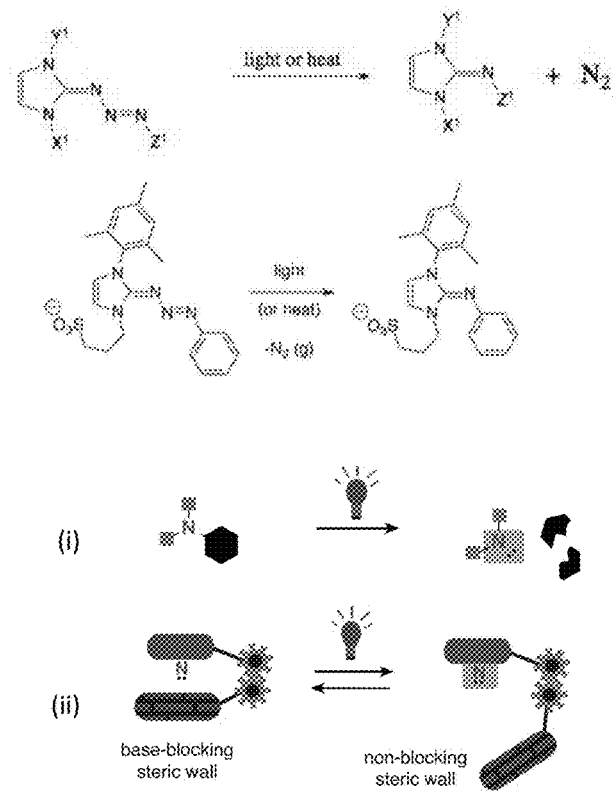
FIG. 4A shows light catalyzed cleavage of triazabutadiene molecules.
Figure 4B:
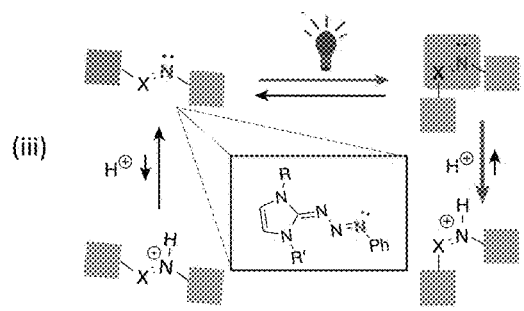
FIG. 4B shows photochemically generated bases. (i) A masked base may decompose to reveal a basic nitrogen atom upon exposure to light; (ii) The basic nitrogen atom of a molecule obscured by a steric wall may be reversibly swung away in a photochemically triggered fashion; (iii) The intrinsic basicity of a nitrogen-containing functional group may be altered by a photochemical event.

In some embodiments, light increases the rate at which the triazabutadiene molecule breaks down (into the cyclic guanidine species and the diazonium species) (see FIG. 4A). The present invention features triazabutadienes that, upon photo-irradiation, may be rendered more basic in a reversible fashion. Referring to FIG. 4B, for reference, a protecting group of a masked base may decompose to reveal a basic nitrogen atom upon exposure to light. Or, a basic nitrogen atom of a molecule obscured by a steric wall may be reversibly swung away in a photochemically-triggered manner. The present invention shows the intrinsic basicity of a nitrogen-containing functional group may be altered by a photochemical event.

Figure 5A:
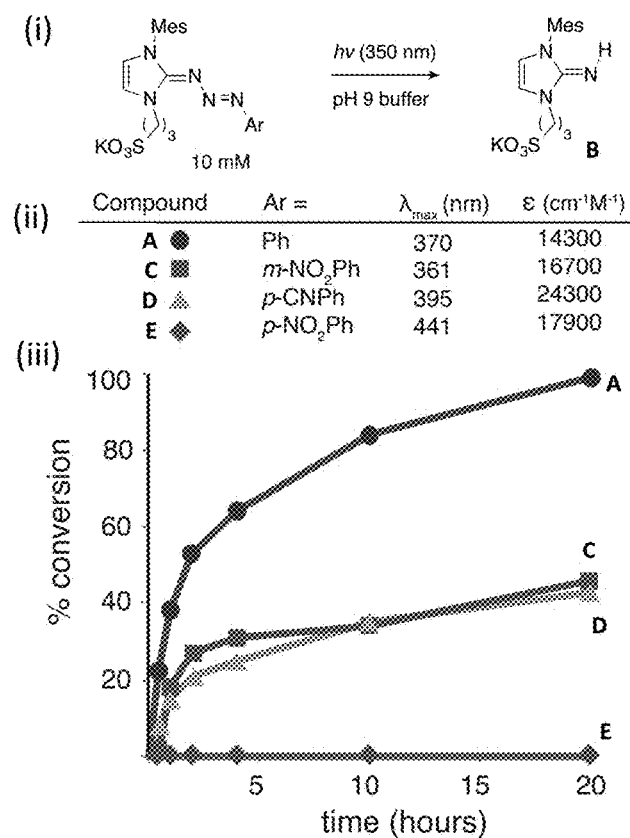
FIG. 5A shows time-dependent photo-induced degradation of triazabutadienes. (i) The reaction was monitored by comparing starting materials (A, C, D, and E) with product (B); (ii) Peak absorption and extinction coefficients for all of the compounds were excitable by the UV source used; (iii) Time-dependent conversion of compounds was measured by NMR integration.

Referring to FIG. 5A, in some embodiments, triazabutadiene molecules of the present invention may readily photoisomerize to a more reactive Z-form. As an example, an aqueous solution of Compound A was irradiated with a simple hand-held UV lamp ("365 nm," measured at 350 nm). Consumption of Compound A was observed after only a few hours. The non-irradiated reaction under similar conditions was stable for days as partial degradation rapidly renders the solution mildly basic. Without wishing to limit the present invention to any theory or mechanism, it was hypothesized that if a two-electron process were happening, then Compound A-Z would be more basic than Compound A-E. A 1.0 N NaOH solution of Compound A was treated with light. At pH 14, Compound A was stable for weeks in the dark; it was surprisingly discovered that near complete consumption of starting material after 20 hours of constant irradiation occurred. NMR analysis of samples post-irradiation showed cyclic guanidine Compound B. Evidence of a benzene diazonium species or phenol/azobenzene products derived therefrom was not observed. Benzene diazonium ions also absorb UV light to expel nitrogen and generate a benzene radical. In order to resolve if the initial cleavage undergoes a radical homolytic mechanism versus a two-electron heterolytic mechanism, a trapping experiment using resorcinol was conducted. (Resorcinol was chosen because it can serve a dual role as a radical scavenger and a trap benzene diazonium species that could be formed.) An excess of resorcinol was added to a pH 9 borate-buffered solution of Compound A and the mixture was irradiated with light. The known azobenzene, Sudan Orange G, was formed in a 65% yield (versus 4% for the non-irradiated reaction). Derivatives of Compound A were made to examine the effects of electronic perturbations on the light-induced degradation. Electron deficient aryl rings are more stable at lower pH, and this trend generally holds true for the photochemical reactions as well. A buffered borate solution was chosen due to its alkaline nature and lack of complicating signals in the NMR experiment. Compounds C-E all have absorption spectra that are well within the range of the UV lamp (see FIG. 4C(ii)). Both m-$NO_2$ (Compound C) and p-CN (Compound D) had similar rates of reaction, both slower than Compound A. To rule out other effects associated with possible heating or interactions of the buffer, p-$NO_2$ derivative Compound E was irradiated because of its significantly red-shifted spectrum. Compound E absorbed in a range that was not irradiated with the UV lamp and as such was recalcitrant to degradation (see FIG. 5A(iii)).

As previously discussed, poorly (or non-) buffered aqueous solutions could become more basic as a function of time due to the degradation to Compound B and the aryl diazonium species. Without wishing to limit the present invention to any theory or mechanism, it is believed that the cause of the increase in pH is Compound B, which acts as a base. It was found that reactions slowed and eventually stopped once the pH had risen to around 9. Without wishing to limit the present invention to any theory or mechanism, it was hypothesized that by driving the reaction to completion with light, it would be possible to increase the pH beyond this dark-reaction imposed wall (analogous FIG. 4B(ii)). Using NMR and a pH meter, it was observed that the pH of a solution of Compound A irradiated with UV light rose in a time-dependent manner.

In an effort to examine the rate order for the pH-increasing reaction more carefully, in situ, real-time pH measurements were acquired. Compound A was dissolved in water and the pH of the solution was adjusted to 9 such that it would not form Compound B in the absence of light. Upon exposing the solution to 350 nm light, it was surprisingly discovered that the solution rapidly spiked up to a pH of ~10 over the course of several minutes, and only upon much longer exposure slowly became more basic. This spike was not at all consistent with the model of the pH increase being solely linked to the concentration of Compound B being generated. Moreover, previous NMR studies showed that much more time was required to afford a pH change commensurate with this apparent level of degradation.

Figure 5B:
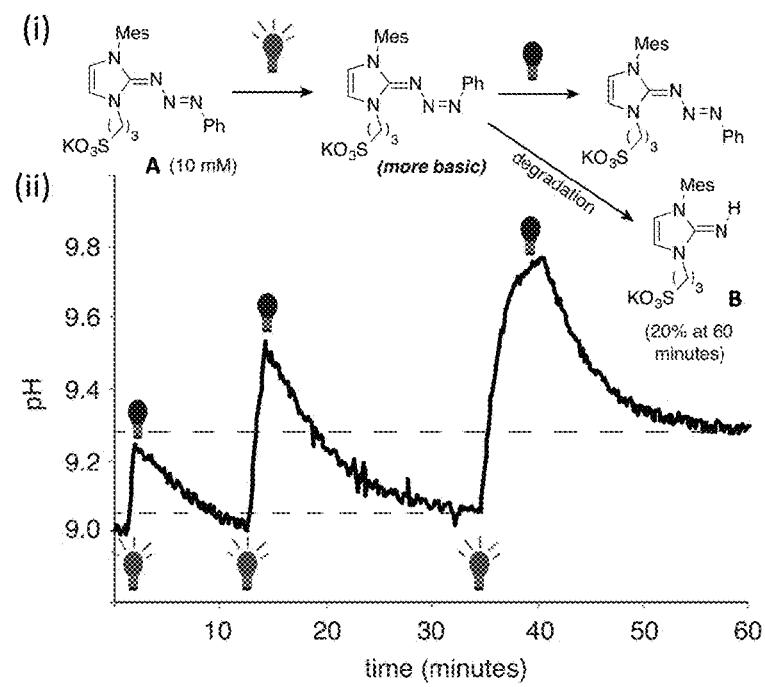
FIG. 5B shows (i) Compound A is rendered more basic upon exposure to light; that basicity recovers (to some extent) in the absence of light; (ii) Oscillating UV irradiation provides a saw-tooth pH trend over time.

Without wishing to limit the present invention to any theory or mechanism, it was hypothesized that the rapid pH increase that was observed was not attributed to Compound B, but instead a result of the Z isomer being significantly more basic than the E isomer (see FIG. 5B(i). A sample was irradiated and then the light was turned off once the pH of the solution started to increase noticeably. As the sample thermally reverted to the more stable E form, the pH of the solution dropped as well (see FIG. 5B(ii)). The experiment was repeated with increasing times of irradiation, and a saw-tooth pattern was obtained. The process was not completely reversible due to some degradation to Compound B. Indeed, triazabutadiene Compound A can serve a dual role of being a photo-masked base (see FIG. 4B(i)), and a base whose intrinsic functional group properties are altered photochemically (FIG. 4B(iii)).

Figure 5C:
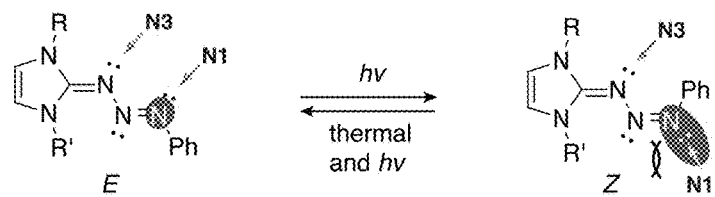
FIG. 5C shows the lone-pair of electrons on the N1 nitrogen atom becomes more electron-rich upon isomerization from E to Z.

This phenomenon via an isomerization-induced $pK_b$ change was surprisingly discovered by the inventor. Without wishing to limit the present invention to any theory or mechanism, unlike the case where Hecht's compound is rendered basic upon irradiation by way of moving of a steric wall (see FIG. 4B(ii), it is unlikely that steric factors play a significant role in this chemistry, especially in water. It is possible that the E-isomer has alternating "non-π involved" lone pairs of electrons, whereas the Z-isomer has two adjacent "non-π involved" lone pairs of electrons (see FIG. 5C). The electronic repulsion from these renders N1 much more electron rich in Z-isomer and thus a stronger Lewis base.

Referring to FIG. 5A(iii), Compound C and Compound D were examined in an effort to find a base that was reversibly basic but also more resistant to degradation. In both cases, a slow subtle change to the pH was observed, but none as dramatic and rapid as Compound A. Without wishing to limit the present invention to any theory or mechanism, it is believed that this may be due to factors such as (a) faster thermal isomerization to the E isomer such that a build up of the Z isomer is not possible; (b) the electron-deficient triazabutadienes are less basic to begin with, so a transition is not observable in the operating pH range.

It is possible that Compound A may be useful as a photo-catalytic base in the context of organic reactions. With limited solubility in all but DMSO, the stability of Compound A was tested. As noted previously, Compound A is quite stable to an excess of acetic acid in DMSO, showing only 12% degradation over 14 hours at room temperature. Upon irradiation with light, Compound A in presence of acetic acid completely fell apart over the same time frame. To confirm that this was due to the acid, a solution of Compound A (in pure DMSO) was irradiated. After four hours of constant irradiation in acid-free DMSO, an E:Z ratio of nearly 50:50 was observed. Moreover, unlike in water, the thermal reversion from Z to E is slow in pure DMSO with a half-life on the order of days. Attributing this to lack of protonation, a control in MeOD was run, and a first-order thermal isomerization was observed with a rate of $3 \times 10^{-5}$ s$^{-1}$ ($t_{1/2}$~6.4 hours), in addition to some degradation to Compound B.

Figure 5D:
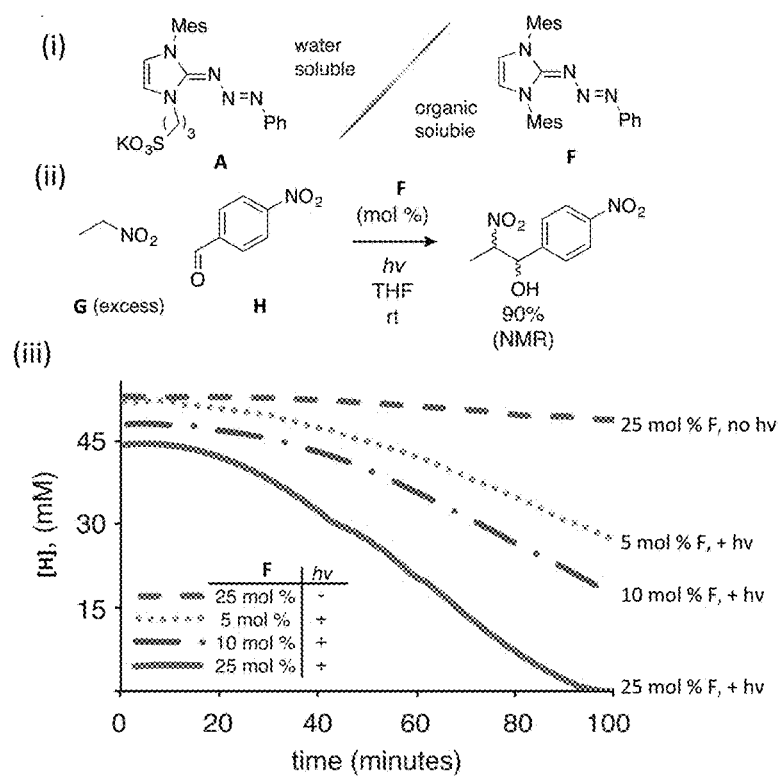
FIG. 5D shows the use of the photobase as a catalyst. (i) Structures of water-soluble Compound A versus organic soluble Compound F; (ii) The Henry reaction between Compound G and Compound H was carried out at room temperature and varying amounts of catalyst; (iii) The reactions were monitored by ReactIR™, following consumption of aldehyde Compound H.

Referring to FIG. 5D, due to the limited organic solubility of Compound A, Compound F (FIG. 5D(i)) was synthesized. With Compound F, a similar light-induced acid sensitivity was observed in DMSO (and slow thermal isomerization). Based on the apparent $pK_b$ of Compound F, $pK_a$ were matched to condensation substrates. A Henry reaction between nitroethane (Compound G) and p-nitrobenzaldehyde (H) was chosen to demonstrate the virtues of Compound F (FIG. 5D(ii)). The reaction between Compound G and Compound H occurred rapidly at room temperature in a light and catalyst dependent manner (FIG. 5D(iii)). The reaction with 25 mole % Compound F in the absence of light was exceedingly slow. Likewise, the reaction with light but no catalyst also failed to proceed. The cyclic guanidine was not observed during a post-reaction analysis of the components from a 25 mole % Compound F run, indicating that the Z-isomer of Compound F is likely to be the catalytically active species in solution. Slow thermal isomerization back to the E-isomer in aprotic organic solvents together with a fast overall reaction attempts to adjust the reaction rate prior to consumption of Compound H. Interestingly, the reaction catalyzed with Compound F was significantly faster than the same reaction reported by Hecht. This may provide evidence that Compound F-Z is more basic than Hecht's blocked trialkylamine.

As previously discussed, the present invention features methods of breaking down triazabutadiene molecules by subjecting the molecule to light. The light may, for example, include wavelengths of about 400 nm. The present invention is not limited to wavelengths of 400 nm or about 400 nm. For example, in some embodiments, the wavelength is from 350 nm to 400 nm (e.g., 370 nm). In some embodiments, the wavelength is from 360 nm to 410 nm. In some embodiments, the wavelength is from 330 nm to 420 nm. In some embodiments, the wavelength is from 340 nm to 430 nm. In some embodiments, the method comprises subjecting the molecule to a low pH and to light.

As previously discussed, light-promoted reactivity and light-facilitating E/Z isomerization has been observed. In some embodiments, a system such as a UV-LED pen may be used for these reactions, however the present invention is not limited to a UV-LED pen and may utilize any appropriate system. The UV-LED pens may allow for relatively narrow bandwidth irradiation of these compounds (but are not limited to these bandwidths). The color of the bulk material shifts as a result of electronic perturbations to the aryl azide starting material. For example, nitro derivative Compound 6e of FIG. 6G is rust-red, versus an orange phenyl Compound 6c of FIG. 6F) and yellow-orange methoxy Compound 6d of FIG. 6G. It may be possible for selective irradiation of a complex mixture in an orthogonal sense. These experiments may be performed in basic aqueous solutions to maintain the solvation properties of water while also preventing the degradation pathway stemming from protonation. These experiments are not limited to basic aqueous solutions.

Without wishing to limit the present invention to any theory or mechanism, it may be considered advantageous that the breakdown of the triazabutadiene molecule is irreversible.

III. Synthesis of Water-Soluble Triazabutadiene Molecules and Experimental Examples Synthesis of 1-mesityl-1-H-imidazole: To a solution of 2,4,6-trimethylaniline (1.35 g, 10.0 mmol) in methanol (15 mL) was added a solution of glyoxal (40%) (1.14 mL, 40% in water, 10. mmol). The mixture was stirred at room temperature until a solid formed. Thereafter, solid ammonium chloride (1.07 g, 20 mmol), formaldehyde (37%) (1.6 mL 37% in water, 60. mmol) and methanol (40 mL) were added, and the mixture was heated to reflux for one hour. After the hour, phosphoric acid (1.4 ml of an 85% solution) was added drop wise and the mixture was refluxed for an additional eight hours. Upon cooling to room temperature ice (30 g) was added and the solution was brought to a pH of 9 with potassium hydroxide (40% in water). The following mixture was extracted repeatedly with diethyl ether. The ether phase was dried over magnesium sulfate and solvent removed in vacuo to form a brown solid which was filtered and washed with hexanes to give the product (0.785 g; 42%). 1H NMR (500 MHz, CDCl3): δ 7.45 (t, J=1.1 Hz, 1H), 7.25 (t, J=1.1 Hz, 1H), 6.99 (dp, J=1.3, 0.7 Hz, 2H), 6.91 (t, J=1.3 Hz, 1H), 2.36 (t, J=0.7 Hz, 3H), 2.01 (t, J=0.6 Hz, 6H). 13C NMR (126 MHz, CDCl3) δ 138.80, 137.47, 135.42, 133.40, 129.55, 128.96, 120.02, 21.03, 17.33. (see Liu, J. et al. Synthesis 2003, 17, 2661-2666).

Synthesis of 3-(1-mesityl-1H-imidazol-3-ium-3-yl) propane-1-sulfonate (see FIG. 6F): To a solution of 1-mesityl-1-H-imidazole (1.00 g, 5.36 mmol) in toluene (30 mL) was added 1,3-propanesultone (1.00 g, 8.18 mmol) and the mixture was heated to reflux overnight. The mixture was allowed to cool to room temperature and the off-white precipitate collected by filtration. The precipitate was further washed with diethyl ether and dried using a vacuum oven to yield a solid (1.40 g; 84%). 1H NMR (500 MHz, D2O): δ 8.92 (t, J=1.6 Hz, 1H), 7.75 (t, J=1.8 Hz, 1H), 7.49 (t, J=1.8 Hz, 1H), 7.06 (q, J=0.8 Hz, 2H), 4.44 (t, J=7.1 Hz, 2H), 2.39-2.31 (m, 2H), 2.25 (s, 3H), 1.96 (s, 6H). 13C NMR (126 MHz, D2O) δ 141.42, 136.54, 134.64, 130.74, 124.34, 123.00, 48.18, 47.17, 25.03, 20.17, 16.29.

Synthesis of Potassium 3-(3-mesityl-2-(phenyltriaz-2-en-1-ylidene)-2,3-dihydro-1H-imidazol-1-yl) propane-1-sulfonate (see FIG. 6G): To a slurry of 3-(1-mesityl-1H-imidazol-3-ium-3-yl)propane-1-sulfonate (50 mg, 0.16 mmol) in dry THF (6 mL), was added a solution of phenyl azide in THF (0.16 mL, 1 M, 0.16 mmol). To the solution was added KO-t-Bu (24 mg, 0.21 mmol) in one portion and the resulting mixture was stirred under argon for 4 hours. Hexanes (1 mL) was then added and the reaction mixture was filtered. The solvent was removed and the residue taken up in a minimal amount of DCM and on trituration with hexanes, pure product was obtained by filtration as a yellow powder (61 mg, 81%). 1H NMR (500 MHz, DMSO-d6) δ 7.32 (d, J=2.4 Hz, 1H), 7.07-7.02 (m, 4H), 6.99-6.94 (m, 1H), 6.84 (d, J=2.4 Hz, 1H), 6.51-6.47 (m, 2H), 4.09 (t, J=7.1 Hz, 2H), 2.34 (s, 3H), 2.12-2.04 (m, 2H), 1.95 (s, 6H). 13C NMR (126 MHz, DMSO-d6) δ 152.19, 151.13, 137.94, 136.15, 134.31, 129.31, 128.60, 125.26, 120.90, 117.61, 117.24, 48.52, 45.05, 25.80, 21.06, 17.95.

Using the procedures described herein, the p-methoxy and p-nitro analogs (from the p-MeO aryl azide and p-NO2 aryl azide) were also prepared.

For decomposition experiments, buffers were made to the appropriate pH in a 9:1 mix of H2O:D2O. These solutions were added to the compound being assayed such that the buffer capacity was at least 10 fold the concentration of the compound. Some experiments used 5 mg compound in 0.5 mL of buffer. These were immediately inserted into an NMR instrument and scans were taken at even time intervals to calculate the half-life of the compound based on integration.

As another non-limiting example, an azide (e.g., NHS-azide) to N-heterocyclic carbene (NHC) route may be used to synthesize triazabutadiene molecules (e.g., see FIG. 6C). For example, as shown in Compound 4 of FIG. 6D, a triazabutadiene molecule was synthesized from dimethyl imidazole derived NHC and phenyl azide. When the triazabutadiene molecule (Compound 4) was treated with methanolic HCL, a rapid color change occurred. This change was confirmed to coincide with diazonium formation by trapping the reactive species with resorcinol to provide known diazo dye Sudan Orange G. When the triazabutadiene molecule (Compound 4) was treated with the much less acidic acetic acid, the same product was obtained. Compound 4 was not water-soluble.

To render the triazabutadiene water-soluble, methyl imidazole was alkylated with propane sultone to provide the Zwitterionic NHC precursor Compound 5a (see FIG. 6E). Formation of the NHC under basic conditions in the presence of phenyl azide yielded the highly water soluble Compound 6a (see FIG. 6E). Compound 6a was highly colored, so its pH dependence was studied using UV/Vis. The reactions were not only pH-, but also scan-frequency dependent. Upon finding this, the stability of Compound 6a was studied in D2O in the dark using NMR. Even in the dark it was unstable, but not in the diazonium-forming way. Both Compound 6b and a more hindered mesityl (Mes) substituted Compound 6c (see FIG. 6E) were synthesized to stabilize what was initially considered to be a rearrangement pathway that could be blocked by steric repulsion. Compound 6c was the most stable of the three (less than 10% consumed after 24 hours versus 50% for Compound 6a and Compound 6b). It is not yet clear that the hypothesis of a simple rearrangement was correct. Dissolution in 0.1 N NaOH rendered all compounds stable (no detectable degradation after 24 hours in the dark).

As mentioned above, Compound 6c was reasonably stable in pure D2O. Upon adjusting the pH to 5 with HCl, a rapid initial consumption of Compound 6c to Compound 7 (see FIG. 6E) and a benzenediazonium salt was noted. After this initial burst of reactivity, a slowing and apparent arresting of the reaction was noted. At this pH the hydronium was the limiting reagent. All future reactions were run in buffers with a buffer capacity sufficient to maintain a large excess of hydronium ions. The experiments were performed in 90:10 H2O:D2O buffered solutions to minimize considerations of pH vs. pD. The decomposition to diazonium salts and Compound 7 was measured as a function of pH in phosphate/citrate buffers from pH 4-7 and in a phosphate buffer from pH 6-8. All runs provided linear correlations of concentration and time, indicating a pseudo-zero order reaction (first order with respect to hydronium ion with a large excess of hydronium ions). While the peaks for Compound 7 remained constant, the peaks associated with Compound 6c drifted downfield as the reaction progressed. This drifting was highly reproducible across samples and buffers, but the underlying cause is not understood at this time. A sigmoidal correlation between rate and buffer pH centered at pH 6 was obtained. When resorcinol was not added to consume the diazonium species, 4-phenylazophenol (Compound 8) was observed (see FIG. 6F). Compound 8 came from the decomposition of one diazonium ion to phenol followed by reaction with a second diazonium ion. The instability of Compound 6c in a pH 7 phosphate buffer was surprising given the stability in D2O. Compound 6c was tested in a non-buffered 90:10 H2O:D2O solution and observed only >7% after 6 hours.

To further examine the reactivity of this class of compounds, variants Compound 6d and Compound 6e were synthesized (see FIG. 6G). It was hypothesized that the p-methoxy and p-nitro analogs (Compound 6d and Compound 6e, respectively) would display different reactivity profiles. It was observed that in pure D2O, 26% of Compound 6d was consumed after 24 hours in the dark at room temperature as compared with Compound 6e, which was stable to within the detection limit of NMR. Preliminary data shows that Compound 6d undergoes decomposition to the diazonium species more rapidly than Compound 6c in pH 5, 6, and 7 phosphate/citrate buffer (rates of 2.0×10-5, 1.0×10-5, and 0.53×10-5 M/s, respectively). Upon attempting the same study with Compound 6e it rapidly precipitated out of solution across the same pH range. After collecting the precipitate and dissolving it in deuterated methanol, no change was observed from a sample of Compound 6e that had never been exposed to a buffered solution. Treatment of this methanolic Compound 6e with HCl led to an immediate color change and diazonium formation was confirmed by trapping with resorcinol. It is possible that: 1) that the sodium salt of Compound 6e is much less soluble than the potassium salt; or 2) with different solvating ions present the sulfonate interacts with the electron-poor N2 nitrogen atom of the triazabutadiene to break conjugation and form an insoluble complex (this is backed by a reversible color change of the starting rust-red solid, to the light yellow precipitate). Note that the p-nitrobenzenediazonium salts are reported to have the best labeling efficiency of tyrosine residues on proteins.

The influence of solvated ions on reactivity was studied. In water, or a heavy water/water mixture, a near-zero rate of diazonium salt formation was observed, yet in solutions buffered to pH 7 and even pH 7.4 an increase in the reaction rate was observed. To assess the role of the anionic component, the reaction in the presence of a range of buffers while holding the pH constant will be observed. Buffers include but are not limited to those expected to have the most diverse properties, e.g., MES, a Zwitterionic morpholino sulfonic acid, and imidazolium chloride, the conjugate acid of a mild base, can both buffer a solution at pH 6.5, but ionic species in solution would be dramatically different. The metals in solution could well be acting as Lewis acids to activate our molecule. A range of metal halide salts dissolved in pure water at varying concentrations will be screened.

Note that all of the compounds in the 6 series (FIG. 6E, FIG. 6F, and FIG. 6G) have a built-in sulfonate to confer solubility. It is possible that this functional group could be serving an important role by effecting the localization of metals, directing them to interact with the nitrogen atoms of the triazabutadiene and thus alter the reactivity of the compound. This may be happening with Compound 6e to such an extreme that the compound is no longer soluble. This concept of a directed metal binding on triazabutadienes was observed, albeit in an organic environment. Referring to FIG. 6H, to study the role of the side chain, the imidazole core will be alkylated (see Compound 9) with either butane sultone to provide imidazolium (Compound 10) and triazabutadiene (Compound 11), or a dialkyl aziridinium salt to provide the analogous Compound 12 and Compound 13 which invert the expected charge on the side-chain. The extra methylene in Compound 11 as compared with Compound 6 may alter the way that the side-chain bites back on the triazabutadiene. The tertiary amine will be protonated at physiological pH and as serve to invert the charge of the side arm. Without wishing to limit the present invention to any theory or mechanism, a potential bonus of Compound 13 is that the basic nitrogen may help localize this compound in the most acidic subcellular compartments much like LysoTracker™ dyes.

Regarding the role of mesityl group in reactivity, it is possible that a function of the mesityl in triazabutadiene reactivity is to provide a steric wall to prevent side reactions. The NMR of Compound 6c (see FIG. 6F) shows a tale of two hydrogen atoms on the imidazole ring. Without wishing to limit the present invention to any theory or mechanism, it is believed that because the ortho methyl groups prevent coplanar aryl rings, the mesityl group is unlikely to sit in conjugation with the imidazole, but the highly differentiated chemical environments might be explained by: 1) the mesityl π-system deshielding the adjacent hydrogen atom, and 2) the aryl ring having an inductive effect. Changing the p-methyl of the mesityl to electron donating and withdrawing groups may allow the adjustment of the electronic parameters without disrupting the steric bulk.

Figure 7A:
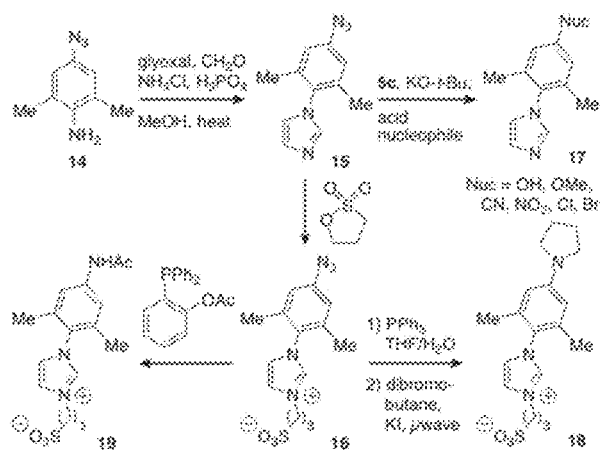
FIG. 7A, FIG. 7B, FIG. 7C, and FIG. 7D show non-limiting examples of reaction schemes involving triazabutadienes.

Referring to FIG. 7A, in some embodiments, synthesis may be performed with known p-azido dimethyl aniline (Compound 14) because it may lead to a wide range of substituted compounds. From imidazole (Compound 15) one can alkylate with 1,3-propanesultone to provide NHC precursor Compound 16, or prior to that one can treat with an NHC to access the wealth of diazonium chemistry to provide Compound 17 in all of its forms. Solvolysis in water or alcoholic solvent may provide a phenol or aryl ether, and copper mediated Sandmeyer-type chemistry may afford cyano, nitro or halogenated aryl species. From imidazolium Compound 16 Staudinger chemistry followed by aniline alkylation may provide Compound 18, or traceless Staudinger-Bertozzi ligation may yield Compound 19. These substrates cover a range of Hammett values while also providing an additional site of attachment to proteins, fluorophores, surfaces, etc.

Figure 7B:
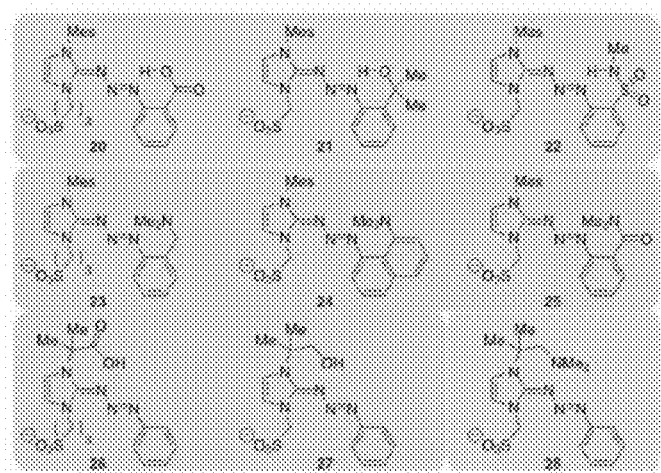
Figure 7C:
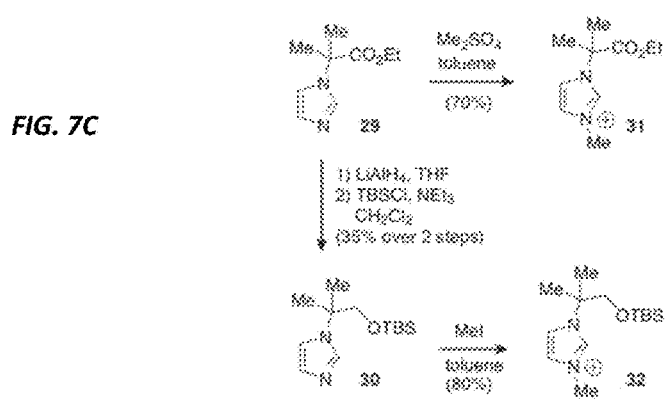

Referring to FIG. 7B, regarding the role of intramolecular hydrogen bond acceptors/donors in reactivity, it may be possible to synthesize a series of triazabutadienes with hydrogen bond donors that possess a range of pKa values (Compounds 20-22). In addition to H-bond donors, it may be possible to synthesize a series of internal bases (Compounds 23-25). It may be possible that bases (e.g., dimethyl amine) positioned near the N1 nitrogen will favor protonation at N3 and thus make the triazabutadiene less stable to acidic media. These compounds are all synthetic targets given a strategy of coupling with aryl azides. The delicate triazabutadiene functional group is installed last under mild conditions. In addition to compounds that are designed to activate/deactivate the N1 nitrogen, it may be possible to synthesize a series of compounds where the N3 nitrogen in most likely to be affected (Compounds 26-28). An NHC with a hydrogen bond donor on a short arm was made. As in FIG. 7C, the synthesis of Compounds 26-28 from known Compound 29 may start with either alkylation to a compound like Compound 31 or reduction and protection to compound 30 followed by alkylation to Compound 32. If the mesityl is absolutely essential for a desired reactivity profile, a H-bond donor/acceptor may be inserted on a methyl group in the ortho position of the mesityl ring.

Figure 7D:
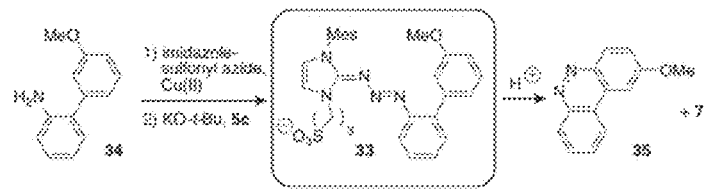

Referring to FIG. 7D, regarding intramolecular trapping of diazonium species, it may be possible to synthesize triazabutadienes with adjacent functional groups that will rapidly consume the diazonium species. For example, Compound 33 contains an aryl ring, positioned ortho to the masked diazonium. The synthesis may start from a diazo transfer reaction to convert aniline Compound 34 to an aryl azide. Coupling with Compound 5c (FIG. 6E) may complete the synthesis. It is possible that following diazonium unmasking an aromatic substitution reaction will occur to provide benzocinnoline Compound 35. Because this reaction is intramolecular one might be able to use a non-activated ring, rendering the ring electron rich. The methyl ether may serve as a site of attachment to chemical cargos. A second type of intramolecular diazonium trap that could be employed is a beta keto ester that is also ortho to the diazonium produced. Beta keto esters are known to react with diazonium species through enol form, and can generate oxo-cinnolines, which are biologically active cores.

IV. Applications and Methods of Use of Triazabutadienes

The triazabutadiene molecules of the present invention may be utilized for a variety of purposes. For example, in some embodiments, the triazabutadiene molecules of the present invention are utilized for a cleavable linkage (e.g., chemoselectively-cleavable linkage) for use in biological/complex settings where rapid, clean cleavage is of interest. In some embodiments, the triazabutadiene molecules are used for systems including but not limited to drug delivery systems, protein-protein interaction systems, pH environment detection systems, etc. Applications of these triazabutadienes may fall under one (or more) categories of reactivity.

a. Diazonium Coupling Applications and Triazabutadiene Probes

Regarding diazonium coupling, the triazabutadiene molecules may be used for applications involving pH-dependent protein coupling. General examples involve methods for detecting protein-protein proximity or protein-protein interactions (in a sample). In some embodiments, the method comprises providing a first protein, wherein the first protein is conjugated with a triazabutadiene molecule according to the present invention. The first protein may be introduced to a sample. In some embodiments, the triazabutadiene molecule encounters a low pH in the sample; in some embodiments, acid is added to the sample to lower the pH appropriately. As previously discussed, in the low pH environment, the triazabutadiene molecule undergoes the irreversible reaction yielding the diazonium species and the cyclic guanidine species. As previously discussed, the diazonium species is adapted to react with a phenol group; thus if there is a nearby protein with a tyrosine residue, the diazonium species may react with it yielding an azobenzene product (often colored, for example the dye, Sudan Orange G is an azobenzene containing dye) that is visually distinct from the triazabutadiene molecule and the diazonium species. As such, detection of the azo dye may be indicative of proximity or interaction of the first protein and the second protein. Thus, in some embodiments, the method comprises adding a second protein to the sample, wherein a tyrosine of the second protein may react with the diazonium species. In some embodiments, the second protein is already in the sample. In some embodiments, a tyrosine or phenol species conjugated to the second protein. In some embodiments, the method comprises introducing to the sample a first antibody specific for a first protein, wherein the first antibody is conjugated with a triazabutadiene molecule according to the present invention. In some embodiments, the method comprises introducing to the sample a second antibody specific for a second protein. In some embodiments, the second antibody comprises a tyrosine. In some embodiments, the second antibody is conjugated with a phenol species. In some embodiments, the method comprises introducing an acid to the sample to appropriately lower the pH of the sample. As previously discussed, in the low pH environment, the triazabutadiene molecule undergoes the irreversible reaction yielding the diazonium species and the cyclic guanidine species. As previously discussed, the diazonium species is adapted to react with a phenol group; thus if the phenol species is nearby, the diazonium species may react with it yielding an azo dye that is visually distinct from the triazabutadiene molecule and the diazonium species. As such, detection of the azo dye may be indicative of proximity or interaction of the first protein and the second protein.

Figure 8:
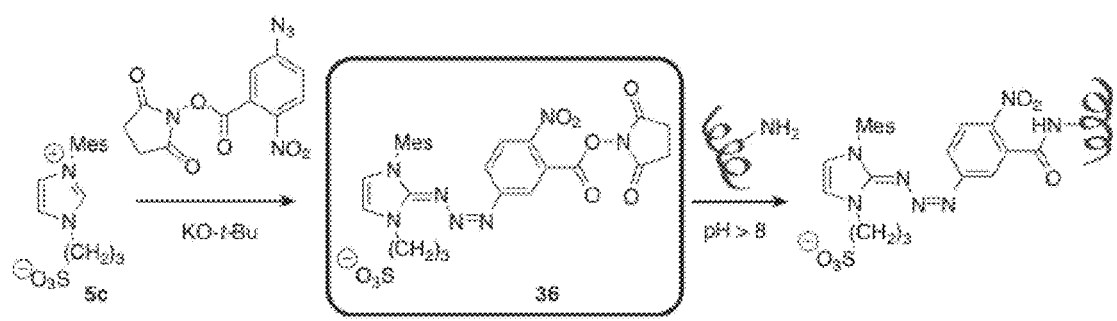
FIG. 8 shows an example of a triazabutadiene molecule adapted to modify a protein.

As a more specific example, the acid-labile reactivity of triazabutadienes may be used to assist in work deducing interaction partners between a virus and endosomally localized host proteins. Upon endosomal acidification a viral-bound diazonium species may be unmasked and this may go on to react with Tyr-containing proteins that are associating with the virus. It is possible that this system could be used to detect or trap an interaction that is relevant at a key point of viral entry, e.g., the fusion of membranes. Herein are non-limiting examples of synthesis of compounds that may be used in such systems, e.g., for modifying the viral surface. Lysine-reactive probes may be used to modify the surface of proteins. Referring to FIG. 8, by synthesizing triazabutadiene Compound 36 bearing an N-hydroxysuccinimide (NHS) ester it may be possible to couple the compound to one of many reactive Lys on the surface of the protein. As previously discussed, a triazabutadiene molecule may be attached to a viral protein (e.g., a purified viral protein). Then, a system such as a cell line (e.g., mosquito cell line, human cell line, or even mosquitoes themselves) may be infected with the viral protein. The infected system can be treated appropriately. The azo dye (e.g., Sudan Orange) may "label" any proteins that interact with or are nearby the viral protein (in the low pH environment). The present invention is not limited to this example. Example 1 below describes the use of triazabutadienes in characterizing viral-host interactions.

Figure 9:
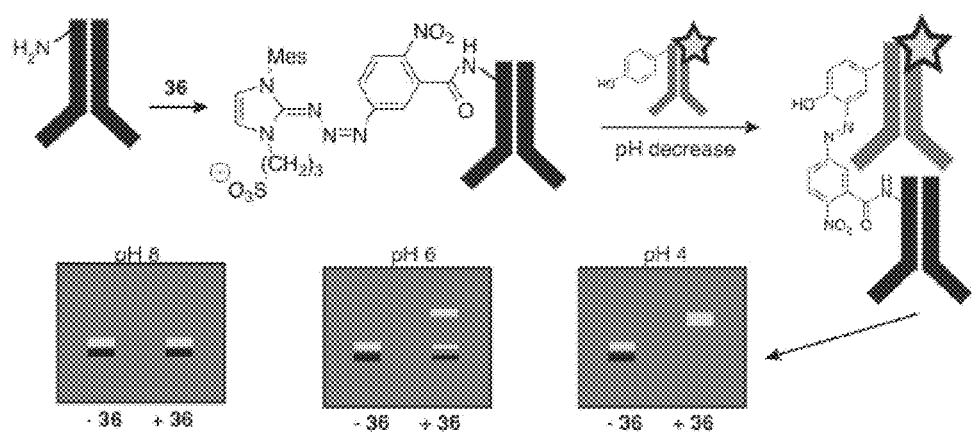
FIG. 9 shows an example of a triazabutadiene molecule conjugated to an antibody, wherein the conjugate is used for labeling a protein of interest.

Lys-NHS conjugation chemistry may work well on the basic side of neutral, which may be beneficial for pH sensitive probes. Referring to FIG. 8 and FIG. 9, Compound 36 may be made in a straightforward fashion from NHC precursor Compound 5c (see FIG. 8) and an aryl azide. It is possible that the steric congestion about the NHC may favor the unencumbered azide over the potentially reactive NHS ester. If the NHS ester presents a problem during the synthesis it is possible to go into the reaction with a carboxylate instead and follow that by a coupling with N-hydroxysuccinimide. If electronically coupling the NHS ester to the aryl system is detrimental to reactivity it is possible to consider inserting an alkyl or, if needed for additional solubility, polyethylene glycol (PEG) linker. As an example, referring to FIG. 9, a monoclonal antibody (e.g., mouse anti-biotin) may be modified with Compound 36. Once the surface is decorated with triazabutadienes, the extent of labeling may be quantified by coupling to resorcinol (or other appropriate alternative) in a low pH solution and the extent of modification may be analyzed by mass spectrometry. This may show the number of reactive triazabutadienes. Following this analysis, a fluorescent goat anti-mouse secondary antibody may be added, and then a gel-shift assay may be used to show that the two antibodies are covalently linked in a pH dependent manner.

Figure 10:
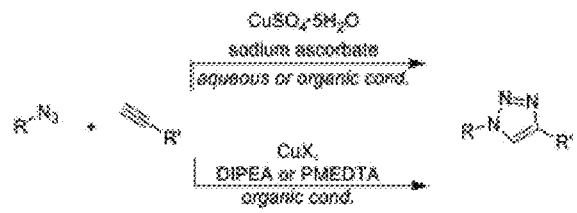
FIG. 10 shows an overview of Cu(II) and Cu(I) click chemistry. DIPEA=N,N-diisopropylethylamine. PMEDTA=1,1,4,7,7-pentamethyldiethylenetriamine.

As previously discussed, the present invention features triazabutadienes that function as cross-linkers, e.g., cleavable cross-linkers. In some embodiments, the triazabutadiene cross-linkers allow for linking components via click chemistry, e.g., via copper-catalyzed azide-alkyne cycloadditions. For example, if a clickable handle (e.g., a terminal alkyne handle) is disposed on the triazabutadiene, it can be used to undergo 1,3-dipolar cycloaddition with an azide handle on a different component (e.g., to yield a 1,4-disubstituted triazole) (see FIG. 10, which shows the click chemistry linking of an azide handle and an alkyne handle forming the 1,4-disubstituted triazole).

The use of triazabutadienes and click chemistry allows for the linking of a wide range of compounds for either chemical or biological applications. Note that in general, in order for the azide-alkyne cycloaddition to occur, it must be activated with a Cu(I) source. In some embodiments, the Cu(I) initiator can come from copper-halide reagents or Cu(II) sources that are reduced in situ. Cu(II) salts such as $CuSO_4$ allow click chemistry to proceed in aqueous conditions with mild reducing agents such as sodium ascorbate (see FIG. 10). Cu(I) halide salts generally require a base/ligand to coordinate the metal insertion and prevent oxidation. Without wishing to limit the present invention to any theory or mechanism, it is believed that copper click chemistry is versatile as it can be performed in a wide range of conditions. This may allow for tunability when it comes to finding the appropriate conditions for triazabutadiene functionalization.

Note that in some embodiments, the alkyne handle is disposed on the triazabutadiene and said alkyne handle can react with an azide handle on a different component. The present invention is not limited to the alkyne handle being deposed on the triazabutadiene. In some embodiments, the azide handle is disposed on the triazabutadiene and said azide handle can react with an alkyne handle on a different component. In some embodiments, both an alkyne handle and an azide handle is linked to the triazabutadiene.

Figure 11A:
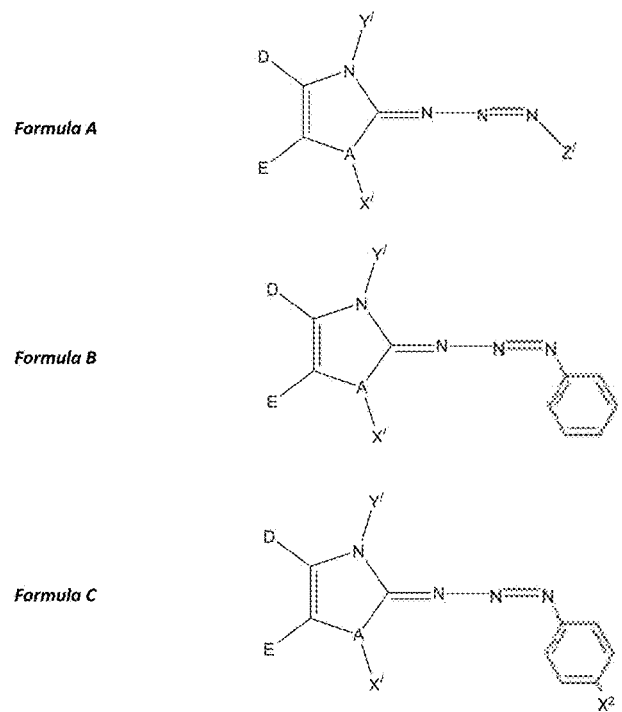
FIG. 11A shows examples of structures of triazabutadienes adapted for click chemistry (see Formula B and Formula C compared to Formula A).

FIG. 11A shows non-limiting examples of structures of triazabutadies adapted for click chemistry, e.g., Formula B and Formula C. In some embodiments, $X^1$ comprises an alkyne handle. In some embodiments, $X^2$ comprises an alkyne handle. In some embodiments, $X^1$ comprises an azide handle. In some embodiments, $X^2$ comprises an azide handle. In some embodiments, the clickable triazabutadiene is according to Formula B, wherein $X^1$ comprises a terminal alkyne handle. In some embodiments, the triazabutadiene is according to Formula C wherein $X^1$ comprises a terminal alkyne. In some embodiments, the triazabutadiene is according to Formula C wherein $X^2$ comprises a terminal alkyne handle. In some embodiments, the triazabutadiene is according to Formula C wherein both $X^1$ and $X^2$ comprise a terminal alkyne handle. In some embodiments, A=S, O, or N; D=H, —CH=CH—CH=E-, halides, cyano, sulfonates, alkyl chain, or trifluoromethyl. In some embodiments, E=H, —CH=CH—CH=D-, halides, cyano, sulfonates, alkyl chain, or trifluoromethyl. Note in some embodiments, the $X^1$ and $Y^1$ may be switched. For example, in some embodiments, A is sulfur, and the alkyne is branched off of the other nitrogen.

Figure 11B:
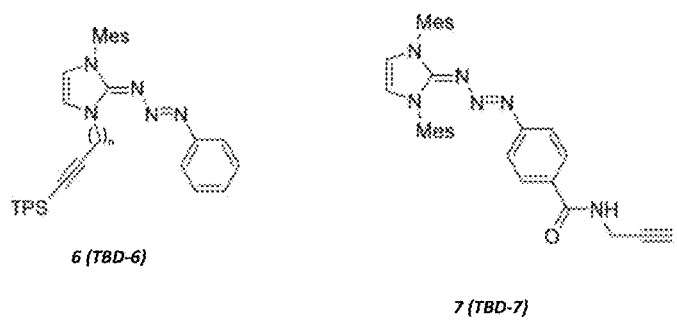
FIG. 11B shows non-limiting examples of triazabutadienes adapted for click chemistry, e.g., triazabutadienes comprising alkyne handles.

As previously discussed, in some embodiments, the triazabutadiene comprises an alkyne handle. FIG. 11B shows TBD-6 and TBD-7, two non-limiting examples of triazabutadienes with alkyne handles. In some embodiments, the alkyne handle is linked to the imidazole portion of the triazabutadiene (TBD-6). In some embodiments the, the alkyne handle is linked to the aryl portion of the triazabutadiene (TBD-7). Note in some embodiments, the alkyne handle comprises a protection group (TBD-6 comprises a protection group). In some embodiments, the protection group comprises chlorotripropylsilane (TPS); however, the protection group is not limited to TPS. For example, in some embodiments, the protection group comprises chlorotrimethylsilane (TMS-Cl), chlorotriethylsilane (TES-Cl), etc.

Figure 12A:
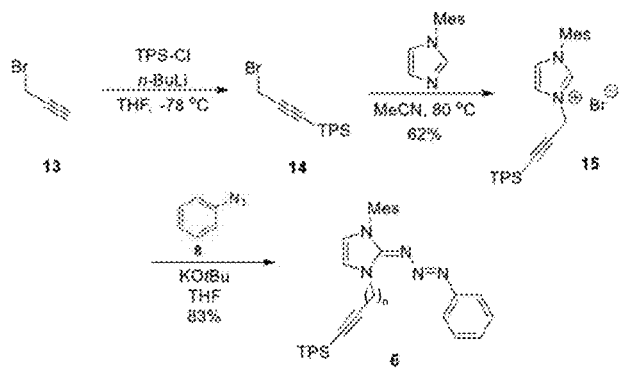
FIG. 12A shows synthesis of a triazabutadiene (TBD-6) comprising a terminal alkyne handle on the imidazole portion of the triazabutadiene. Note in some embodiments, n=1, n=2, n=3, n=4, etc.
Figure 12B:
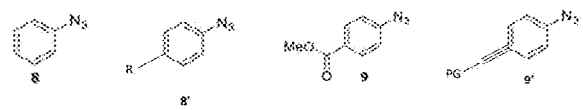
FIG. 12B shows examples of azides for clickable triazabutadiene synthesis, e.g., synthesis of a triazabutadiene such as TBD-6 of FIG. 12A. Note in azide 9', PG stands for protecting group.

The synthesis of TBD-6 (from FIG. 11B) was performed as shown in FIG. 12A beginning with silylation of propargyl bromide (Compound 13). (Protection of the alkyne was necessary due to the similar $pK_a$ values of an alkyne ($pK_a$=25) and the proton on a NHC-salt ($pK_a$=21-24)). Propargyl bromide (Compound 13) was treated with n-butyllithium (n-BuLi) to deprotonate the terminal alkyne to render it nucleophilic so it would react with Chlorotripropylsilane (TPS-Cl) yielding the silyl-protected alkyne (Compound 14). The crude of Compound 14 was only partially purified by flash column chromatography, and was taken to reflux with N-mesitylimidazole in acetonitrile for 2 days to produce the imidazolium salt Compound 15. The coupling of Compound 15 and phenyl azide Compound 8 took place in dry THF. KOtBu was added to generate the NHC to react with the azide and form Compound 6 in moderate yield. This reaction was very moisture sensitive and acquiring best yield in dry conditions. The present invention is not limited to phenyl azide (Compound 8 of FIG. 12A and FIG. 12B). In some embodiments, synthesis of clickable triazabutadienes features alternative azide compounds such as Compound 8' (e.g., Compound) (see FIG. 12B). Note that the methods of using a clickable triazabutadiene according to TBD-6 for click chemistry comprises removing of the protection group (e.g., deprotecting the silyl group). In some embodiments, the use of a compound such as but not limited to tetra-n-butylammonium fluoride (TBAF) in the reaction may allow for deprotecting the silyl group to allow a click reaction to proceed.

Figure 12C:
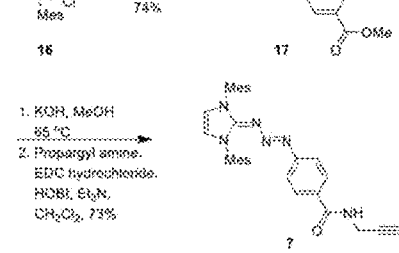
FIG. 12C shows synthesis of a triazabutadiene (TBD-7) comprising an alkyne handle on the aryl portion of the triazabutadiene.

The synthesis of TBD-7 (from FIG. 11B) was performed as shown in FIG. 12C. Bis-mesitylimidazolium chloride salt Compound 16 was deprotonated with sodium hydride (NaH) to generate the reactive NHC species in the presence of p-azido-methylbenzoate Compound 9 to form Compound 17. The K-salt intermediate of Compound 7 underwent 1-Ethyl-3-(3-dimethylaminopropyl)carbodiimide (EDC) coupling with hydroxybenzothiazole (HOBt) in order to form a reactive HOBt ester intermediate. This rendered the carbonyl group highly electrophilic for a nucleophilic attack by propargyl amine to produce the amide bond and the triazabutadiene Compound 7 with a terminal alkyne for click chemistry.

Figure 12D:
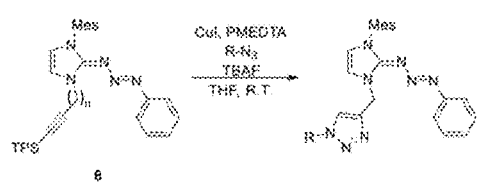
FIG. 12D shows click chemistry with a clickable triazabutadiene (TBD-6). Note in some embodiments, n=1, n=2, n=3, n=4, etc.

FIG. 12D shows click chemistry using a clickable triazabutadiene comprising an alkyne handle (TBD-6). Table 1 below shows examples of R groups attached to the azide handle that is clicked to the clickable triazabutadiene. The triazabutadiene 6, organic azide, CuI, and PMEDTA were in a solution of tetrahydrofuran (THF).

TABLE 1

Synthesis of imidazolium-substituted triazole-triazabutadiene

| Entry | R | Product | Time (hr) | Yield (%) |
|---|---|---|---|---|
| 1 | MeO-C6H4- (11) | 19 | 5 | 56 |
| 2 | n-hexyl (10) | 20 | 2 | 48 |

Figure 12E:
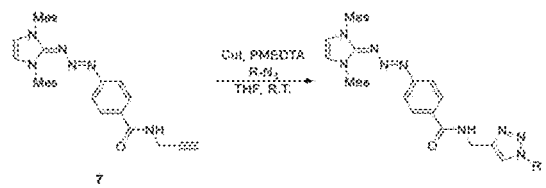
FIG. 12E shows click chemistry with a clickable triazabutadiene (TBD-7).

FIG. 12E shows click chemistry using a clickable triazabutadiene comprising an alkyne handle (TBD-7). Triazabutadiene Compound 7 (TBD-7) was subjected to similar conditions using the same azides (Table 2 below) with a minor alteration. Due to the installation of the alkyne handle after triazabutadiene synthesis, a protection step was unnecessary. The Cu-click reaction proceeded with moderate yields.

TABLE 2

Synthesis of aryl-substituted triazole-triazabutadient

| Entry | R | Product | Time (hr) | Yield (%) |
|---|---|---|---|---|
| 1 | MeO-C6H4- (11) | 21 | 4 | 50 |
| 2 | n-hexyl (10) | 22 | 6 | 73 |

The present invention also features methods of cleaving said triazabutadienes, e.g., cleaving the clickable triazabutadienes that has undergone click chemistry and is in the cross-linking state, e.g., compounds such as the products of the reactions in FIG. 12D and FIG. 12E. In some embodiments, cleavage of the cross-linking triazabutadiene liberates the diazonium species; thus, the present invention also features methods that feature diazonium reactions following cleavage of said linking triazabutadienes.

Figure 13A:
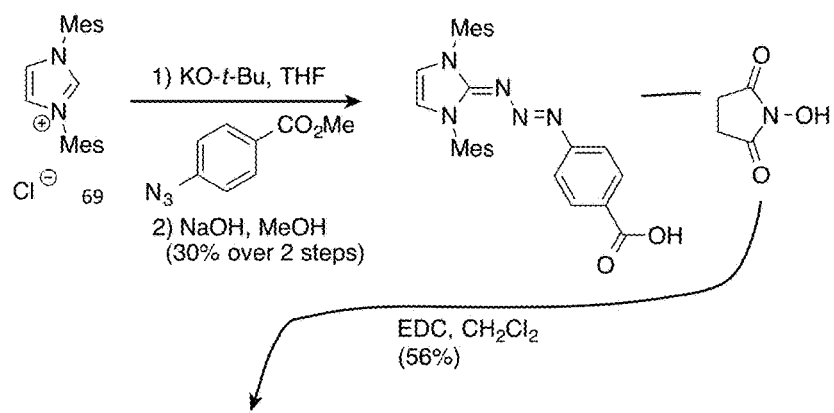
FIG. 13A shows synthesis of a triazabutadiene containing an N-hydroxysuccinimide ester.
Figure 13B:
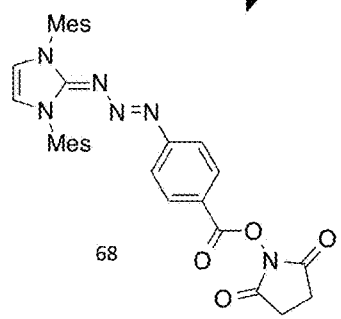
FIG. 13B shows Compound 68.
Figure 13C:
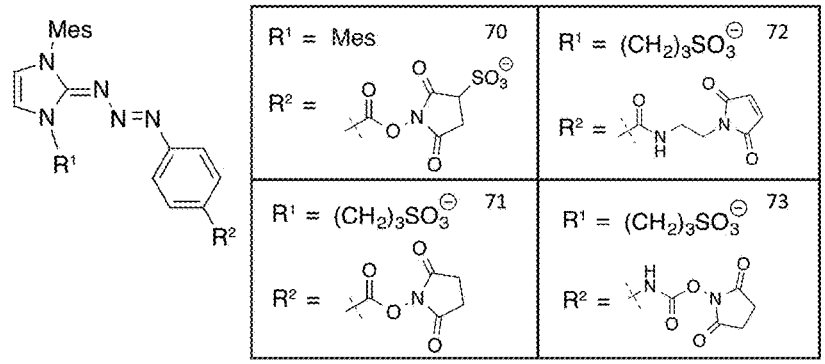
FIG. 13C shows derivatives related to Compound 68.

The present invention also features a lysine-reactive N-hydroxysuccinimide (NHS) modified triazabutadiene, e.g., Compound 68 (see FIG. 13A). This was synthesized from bismestiyl imidazolium, e.g., Compound 69 (FIG. 13B). A series of derivatives is shown in FIG. 13C. Several variants of Compound 68 may be synthesized and tested. For example, Compound 70 with a sulfonate-containing NHS ester may provide a protein modified identically to using Compound 8, but it is may be soluble at higher concentrations, which may enable more rapid labeling of dilute protein samples (such as viral samples). Another sulfonate-containing derivative, Compound 71, may have the effect of adding a negative charge to the surface of the protein that it modifies. Because this is a lysine reactive probe, the change of the charged surface of the protein from positive to negative could have significant impacts. That said, once the triazabutadiene degrades to an aryl diazonium ion, the surface will regain its positively charged nature. A third probe that may be synthesized, Compound 72, contains a cysteine (thiol) reactive maleimide, which may offer a greater degree of selectivity due to the low abundance of surface exposed thiols. This probe may be used in conjunction with proteins that have been mutated to possess a solvent expose cysteine at positions of interest. Based on earlier studies that focused on the electronic-parameters associated with aryl diazonium release rates, the linkage chemistry to the aryl ring may have an effect. The N-linked amide probe, Compound 73, may be used to look at those electronic effects in the context of a complex biological sample.

Figure 14A:
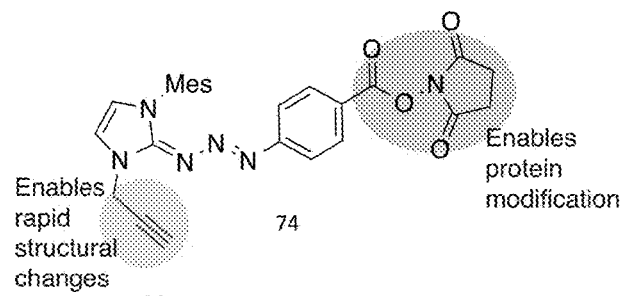
FIG. 14A shows a proposed lysine reactive triazabutadiene that can be rapidly modified in situ by click chemistry.
Figure 14B:
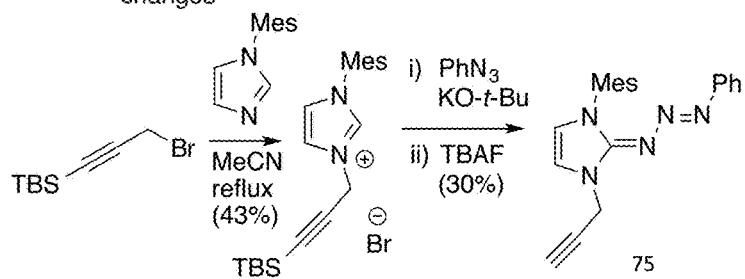
FIG. 14B shows preliminary synthesis of an alkyne containing triazabutadiene Compound 75.

To assess the role of charges and perturbations that the probes have on proteins alkyne-containing triazabutadiene Compound 74 may be synthesized (see FIG. 14A). The alkyne may allow further modification of the scaffold either pre or post protein modification. The proof of concept version of this probe was shown to undergo a Cu(I) catalyzed click reaction with p-azidotrifluoromethylbenzene (FIG. 14B).

Figure 14C:
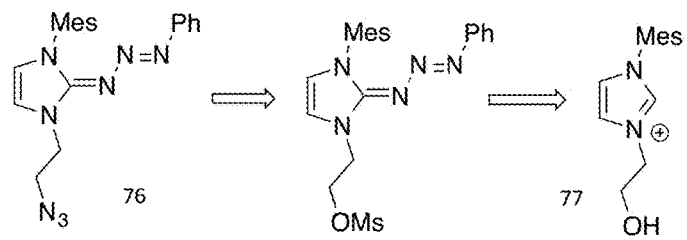
FIG. 14C shows proposed retrosynthesis of azide-containing triazabutadiene Compound 76 from imidazolium Compound 77.
Figure 14D:
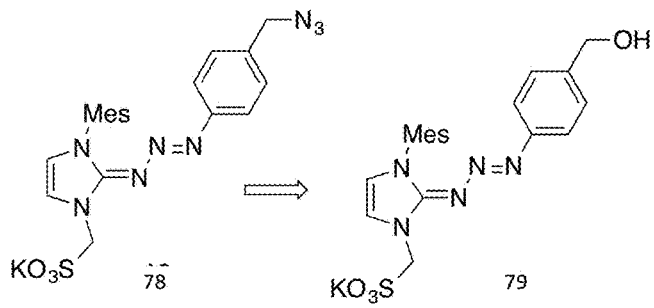
FIG. 14D shows benzylic azide Compound 78 can be made from previously synthesized alcohol Compound 79.

The azide version, Compound 76, may help remove the limits on coupling partners (FIG. 14C). To further expand coupling capabilities, an azide or alkyne on the aryl side of the triazabutadiene, like in Compound 78 (FIG. 14D), may allow for conjugation to alkyne- or azide-modified (respectively) unnatural amino acids, glycans, or other metabolites that are to be studied.

Figure 15:
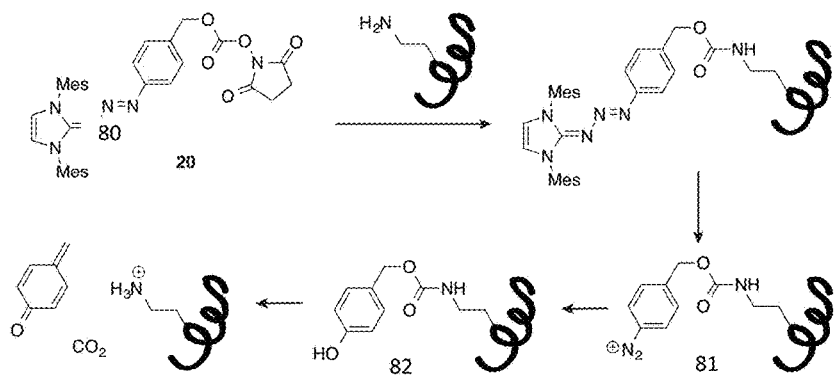
FIG. 15 shows lysine-reactive triazabutadiene Compound 80 is designed to self-immolate to return the starting lysine residue if the resulting diazonium ion, Compound 81, fails to undergo a reaction with tyrosine.

In the absence of a protein cross-linking event, there may be an aryl diazonium, which decomposes to a phenol and remains bound to the lysine. This phenol is likely prone to redox chemistry and as such represents an avenue for complexity during proteomic analysis. A self-immolating triazabutadiene has been designed to circumvent these pitfalls. Referring to FIG. 15, triazabutadiene Compound 80 provides an aryl diazonium (Compound 81), which can go on to react with locally available tyrosine residues, or decompose to phenol Compound 82 if none are available. This phenol will further degrade via quinone-methide chemistry to extrude carbon dioxide and return an unaltered lysine residue.

d. Diazonium Degradation for Cargo or Drug Release

In some embodiments, the triazabutadiene molecules of the present invention may be used in applications involving diazonium degradation to release cargo or drugs. For example, a group of applications takes advantage of the solvolysis of diazonium salts to produce phenolic byproducts. The degradation of diazonium salts to phenols, via aryl cations, is a first-order process that is not pH dependent in the physiological range of pHs. The half-life of this first order process depends on substitution on the aryl ring; the rate for benzenediazonium is ~4 hours. Indeed, the product of this degradation and subsequent azo-dye formation was observed if resorcinol is not put into the buffered NMR experiments.

In some embodiments, the acid-dependent instability of the triazabutadiene molecule may allow for a drug or cargo molecule to be deposited at a desired location and time (e.g., the reaction can be controlled and initiated at a desired time and location). As such, the present invention also features methods of delivering a drug (or a cargo compound) to a subject. In some embodiments, the method comprises providing a triazabutadiene molecule according to the present invention, conjugating a drug (or cargo compound) to the triazabutadiene molecule; and administering the conjugate (the drug/cargo-triazabutadiene conjugate) to the subject. In some embodiments, the method comprises providing a triazabutadiene molecule according to the present invention wherein the triazabutadiene molecule comprises the drug (or cargo compound); and administering the triazabutadiene molecule to the subject. In some embodiments, the diazonium species of the triazabutadiene molecule is part of the drug (or cargo compound). In some embodiments, the drug (or cargo compound) is formed when the diazonium species reacts to a phenol species. In some embodiments, the drug is an anti-cancer drug. The drug (or cargo compound) is not limited to an anti-cancer drug. Any appropriate drug for any appropriate condition may be considered. Likewise, the triazabutadiene molecules may be incorporated into drug/cargo-delivery systems for conditions including but not limited to cancer or other conditions associated with low pH states (e.g., gastrointestinal conditions, sepsis, ketoacidosis, etc.). Non-limiting examples of drugs (e.g., drugs that have a phenolic functional group, which may be masked as prodrugs) include: Abarelix, Alvimopan, Amoxicillin, Acetaminophen, Arformoterol, Cefadroxil, Cefpiramide, Cefprozil, Clomocycline, Daunorubicin, Dezocine, Epinephrine, Cetrolrelix, Etoposide, Crofelemer, Ezetimibe, Idarubicin, Ivacaftor, Hexachlorophene, Labetalol, Lanreotide, Levodopa, Caspofungin, Butorphanol, Buprenorphine, Dextrothyroxine, Doxorubicin, Dopamine, Dobutamine, Demeclocycline, Diflunisal, Dienestrol, Diethylstilbestrol, Doxycycline, Entacapone, Arbutamine, Apomorphine, Balsalazide, Capsaicin, Epirubicin, Esterified Estrogens, Estradiol Valerate, Estrone, Estradiol, Ethinyl Estradiol, Fulvestrant, Goserelin, Fluorescein, Indacaterol, Levosalbutamol, Levothyroxine, Liothyronine, Lymecycline, Mitoxantrone, Monobenzone, Morphine, Masoprocol, Mycophenolic Acid, Phenylephrine, Phentolamine, Oxytetracycline, Rifaximin, Rifapentine, Oxymetazoline, Raloxifene, Tolcapone, Terbutaline, Tetracycline, Mesalamine, Metaraminol, Methyldopa, Minocycline, Nabilone, Nalbuphine, Nelfinavir, Propofol, Rotigotine, Ritodrine, Salbutamol, Sulfasalazine, Salmeterol, Tapentadol, Tigecycline, Tolterodine, Teniposide, Telavancin, Topotecan, Triptorelin, Tubacurarine, Valrubicin, Vancomycin, etc.

In some embodiments, drug delivery systems featuring triazabutadiene molecules may be enhanced with other reactions, e.g., enzymatic reactions. Such additional reactions may help provide appropriate specificity of the drug delivery system or appropriate timing to the drug delivery system.

Figure 16A:
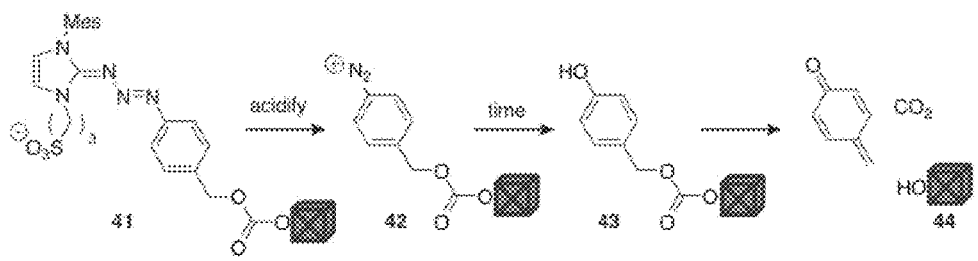
FIG. 16A shows an example of cargo release from a triazabutadiene molecule.

Referring to FIG. 16, the triazabutadiene molecules of the present invention may be used for applications involving benzoquinone methides, e.g., it may be possible to synthesize derivatives that can undergo elimination via para-quinone methide chemistry (see FIG. 16A). Referring to FIG. 16A, after acidification, triazabutadiene Compound 41 may decompose to diazonium salt (Compound 42). This reactive species may decompose to a phenol (Compound 43), which itself decomposes to a quinone methide and may liberate the cargo molecule (Compound 44). It may be possible to modify the electronic properties of the central ring in order to influence the rates at each step. This system is may be useful for these modifications because none of them are expected to affect the cargo. The azide-coupling chemistry may render this amenable to wide variety of chemical cargos. In a biological context these compounds may be able to release their desired cargo upon entry into the endosome, or upon exposure to non-virally relevant acidic environments such as in proximity to cancerous tumors. This type of attachment chemistry may be utilized as a method for drug or detection delivery, and may have an added level of specificity if the system was delivered to a desired location using an antibody or aptamer.

Figure 16B:
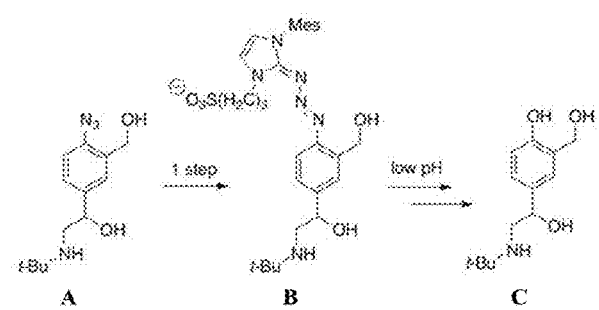
FIG. 16B shows an example of how a prodrug is released.
Figure 16C:
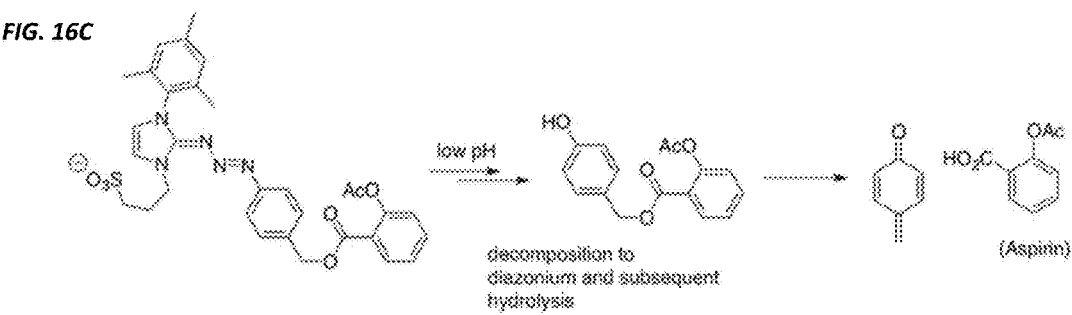
FIG. 16C shows an example of a prodrug comprising a phenolic functional group masked as a triazylidine moiety.
Figure 16D:
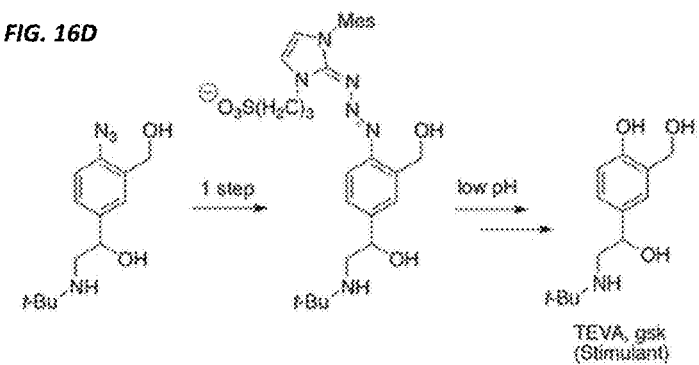
FIG. 16D shows an azide functional group reacted with a carbine to produce an acid labile prodrug comprising a triazylidine moiety.

In some embodiments, $Z^1$ (see FIG. 1, FIG. 16C) is a prodrug comprising a phenolic functional group, wherein the phenolic group is masked as a triazylidene moiety. An example of how a prodrug is released (e.g., in an acidic environment, e.g., in a patient) is illustrated in FIG. 16B. Without wishing to limit the present invention to any theory or mechanism, it is believed that all drugs, such as those approved by the U.S. Food and Drug Administration, that have a phenolic functional group may be masked as a triazylidene moiety.

Referring to FIG. 16B, Compound C is a stimulant that is produced by Glaxo Smith-Kline Beecham pharmaceutical company. The phenolic group of Compound C can be converted to an azide group, e.g., by displacement of the hydroxyl group with an azide group. In some embodiments, the phenolic group is first converted to a suitable leaving group before subjecting to a nucleophilic displacement reaction with an azide group. The resulting azide Compound A is then reacted with 3-(3-mesityl-2-(phenyltriaz-2-en-1-ylidene)-2,3-dihydro-1H-imidazol-1-yl) propane-1-sulfonate to produce triazylidene Compound B. In some embodiments, when Compound B is administered to a patient (e.g., orally or intravenously), the acidic environment of the patient's gastrointestinal tract (if administered orally) or patient's blood plasma (when administered intravenously) decomposes it to generate a corresponding diazonium compound regenerates the phenolic group as illustrated in FIG. 16B. By converting the phenolic group (e.g., the hydroxyl group that is attached to a phenyl ring) to an azide, one skilled in the art having read the present application can readily convert the phenol compound to a triazylidene compound of the invention. Thus, the triazylidene moiety serves as a masking group for a phenolic functional group.

The present invention also features a method for administering a drug comprising a phenolic function group to a subject in need of such a drug administration. In some embodiments, the method comprises converting a drug comprising a phenolic-functional group to a prodrug, wherein said prodrug comprises an acid labile triazylidene moiety; and administering said prodrug to a subject in need of such a drug administration. In some embodiments, the triazylidene compound may also comprise a water solubility conferring moiety and/or $Y^1$ functional group.

The present invention also features a method of converting a drug comprising a phenolic-function group to an acid labile prodrug. In some embodiments, the phenolic-functional group is converted to an azide group. The azide functional group may then be reacted with a carbene to produce an acid labile prodrug comprising a triazylidene moiety (see FIG. 16D).

In some embodiments, a triazabutadiene molecule is conjugated to another molecule (a conjugate molecule), e.g., a protein (e.g., an amino acid such as but not limited to lysine), a lipid, or other appropriate molecule. In some embodiments, the diazonium species part of the triazabutadiene molecule is conjugated to the conjugate molecule. In some embodiments, the cyclic guanidine species part of the triazabutadiene molecule is conjugated to the conjugate molecule. In some embodiments, the triazabutadiene molecule is attached to the conjugate molecule via a linker. Linkers are well known to one of ordinary skill in the art and may include (but are not limited to) a polyether linkers such as polyethylene glycol linkers. In some embodiments, the conjugate molecule to which the triazabutadiene molecule is conjugated comprises an antibody or a fragment thereof. In some embodiments, the conjugate molecule to which the triazabutadiene molecule is conjugated comprises a viral protein.

In some embodiments, the triazabutadiene molecules of the present invention are used for pull-down studies wherein a biomolecule or protein of interest is attached to one side and the other side is appended to something such as but not limited to a small molecule (e.g., hapten such as biotin) or compound. Using biotin as an example, the biomolecule or protein of interest can be pulled down using an avidin bead (which binds strongly to the biotin) and thoroughly washed. This may be useful for protein enrichment. The biomolecule or protein of interest may then be cleaved from the avidin bead by means of reductive cleavage of the triazabutadiene that holds them together. The present invention is not limited to these components, for example this application could also feature the use of a probe (e.g., fluorescent or otherwise) attached to an antibody used to interrogate a complex sample.

In some embodiments, reductive cleavage of triazabutadiene molecules may also be used to cleave unreacted triazabutadienes that did not undergo diazonium formation/reaction chemistry that is associated with a drop in pH (or other mechanism) as described above (a sort of quench for the pH chemistry).

As previously discussed, the diazonium species can react with a phenol species such as resorcinol or other appropriate phenol species. In some embodiments, a phenol species or resorcinol species is conjugated to a protein, e.g., a protein different from the protein to which the triazabutadiene molecule is conjugated, a protein that is the same protein to which the triazabutadiene molecule is conjugated, etc. In some embodiments, the resorcinol species or phenol species that the diazonium species reacts with is the phenol functional group of a tyrosine residue.

c. Other Applications

Figure 17:
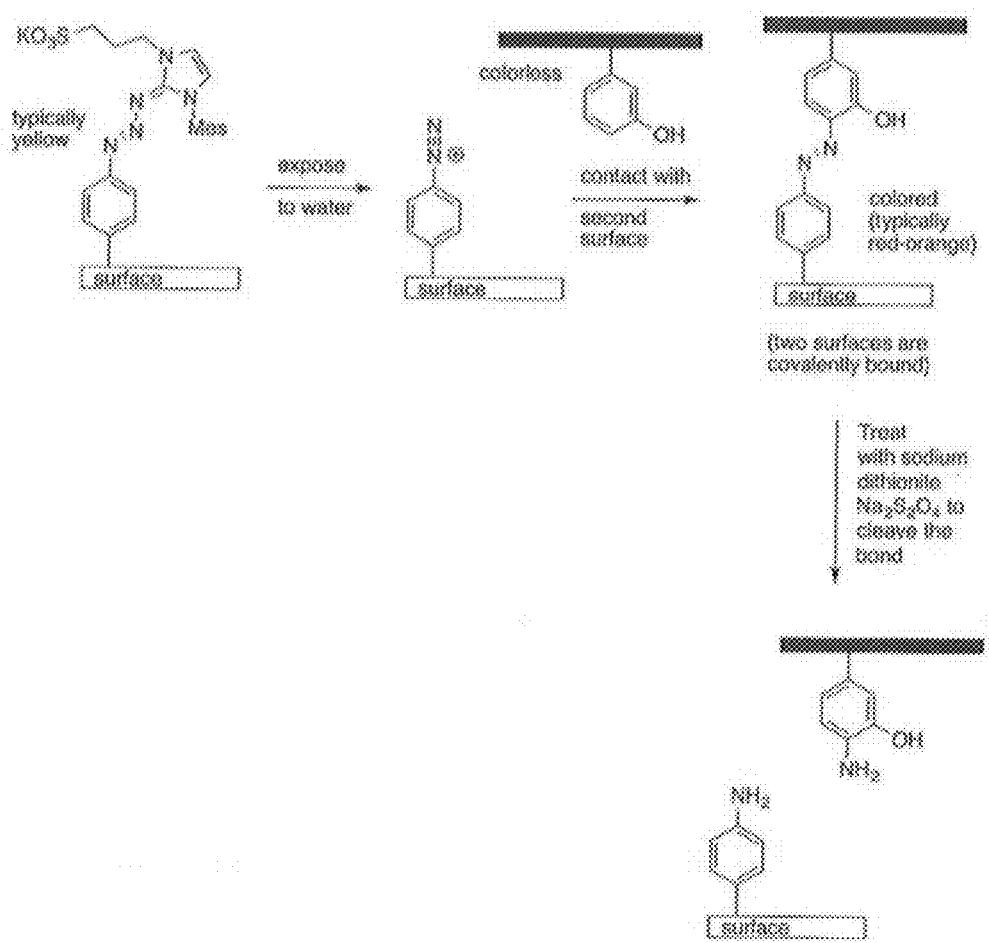
FIG. 17 shows an example of triazabutadiene molecules used as adhesives.

As previously discussed, the present invention features triazabutadienes as adhesives. FIG. 17 shows a triazabutadiene molecule bonded to a first surface. A phenol-containing compound is bonded to a second surface. First and/or second surfaces may include but are not limited to glass, plastic, a biomaterial, or any other appropriate surface, e.g., a surface that allows for linkage chemistry, e.g., the first surface could be any surface that allows for the attachment of a triazabutadiene molecule, the second surface could be any surface that allows for the attachment of a phenol-containing compound. Non-limiting examples of materials also include Tufnol materials such as phenolic cotton laminated plastics, phenolic paper laminated plastics, etc., a phenol formaldehyde resin such as bakelite (or baekelite), etc. As in FIG. 17, the first reaction (wherein the triazabutadiene molecule is exposed to water to result in diazonium species formation) may be performed at room temperature; however, the reaction may be at a different temperature, e.g., depending on the environmental conditions. Without wishing to limit the present invention to any theory or mechanism, it is believed that different temperatures may affect the rate at which the first reaction (wherein the triazabutadiene molecule is exposed to water to result in diazonium species formation) and/or the second reaction (wherein the diazonium species reacts with the phenol-containing compound on the second surface) occurs. FIG. 17 also shows cleavage of the azobenzene linkage upon treatment with the reducing agent sodium dithionite. In some embodiments, the reducing agent is not sodium dithionite but is another appropriate reducing agent. In some embodiments, the surface (e.g., glass, plastic, etc.) is modified, e.g., using an etching mechanism. In some embodiments, photolithography etching may be used to shape the available triazabutadiene molecules. For example, one may intentionally expose certain triazabutadiene molecules to light (e.g., in a pattern via a mask, for example) so as to transition them to the diazonium species; if left unreacted, the diazonium species will then transition to a phenolic compound (as previously described), and thus will be non-sticky or unreactive with the phenol-containing compound on a second surface. This system can allow for the etching away of undesired triazabutadienes.

As previously discussed, the present invention features triazabutadienes as additives in adhesive systems. In some embodiments, triazabutadienes are used with (e.g., added to) adhesives systems such as existing adhesive systems (e.g., epoxy adhesive systems). Epoxy adhesive systems typically comprise an epoxy compound (epoxy resin) and a co-reactant (curing agent or hardener), wherein the adhesive is formed when the co-reactant reacts with the epoxy compound. The present invention features formulations comprising a triazabutadiene and an epoxy compound, wherein the formulation is adapted to react with a curing agent (co-reactant) to form an adhesive. Epoxy resins and curing agents are well known to one of ordinary skill in the art. Examples of epoxy resins include but are not limited to bisphenol A epoxy resins and glycidylamine epoxy resins. Examples of curing agents include but are not limited to amines and thiols. Note that the triazabutadiene can be attached to either the amine or epoxy side. Similarly, the electron-rich aryl (e.g., phenol) can similarly be added to either component (or both).

Figure 18A:
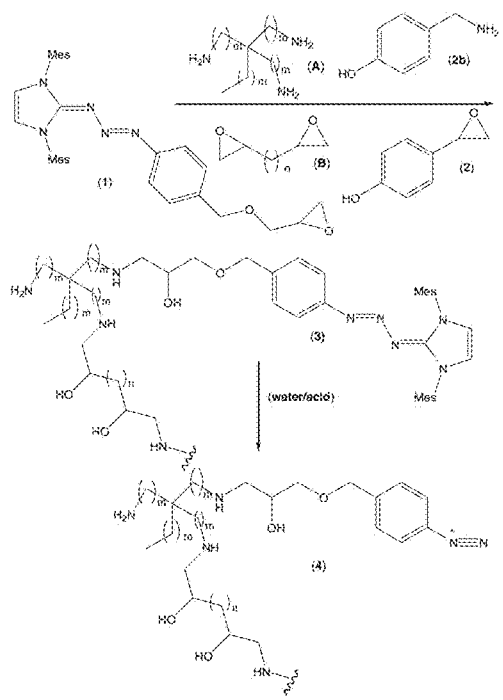
FIG. 18A shows an example of a triazabutadiene comprising an epoxide (Compound 1) that can be added to an epoxy resin (Compound B).

In some embodiments, the triazabutadiene comprises an epoxide (e.g., epoxide or other appropriate epoxy group). A non-limiting example of a triazabutadiene comprising an epoxide is shown as Compound 1 in FIG. 18A. The epoxide triazabutadiene may be mixed with an epoxy residue (Compound B in FIG. 18A), e.g., to generate a formulation. Note that the present invention is not limited to the epoxy residue shown in FIG. 18A. In some embodiments, the formulation (formulation comprising the triazabutadiene and the epoxy resin) further comprises an electron-rich aryl ring group (e.g., phenol or other appropriate group) with an epoxide (see Compound 2). This may help provide additional electron rich aryl rings (e.g., phenol groups) with which the aryl diazonium species can react (subsequent to subjecting the triazabutadiene to appropriate conditions so as to yield said aryl diazonium species). Also shown in FIG. 18A is a non-limiting example of a co-reactant (curing agent). In some embodiments, an electron-rich aryl ring (e.g., phenol group) (see Compound 2b) is added to the co-reactant. As previously discussed, this may help provide additional electron rich aryl rings (e.g., phenol groups) with which the aryl diazonium species can react.

The reaction of the formulation (Compound 1 and Compound B; or Compound 1, Compound 2, and Compound B) and the co-reactant (Compound A; or Compound A and Compound 2b) yields Compound 3, e.g., a polymerized triazabutadiene. Exposure of Compound 3 to water (or other appropriate conditions such as acid) yields the aryl diazonium species (e.g., Compound 4). Compound 4 is available for reacting with electron-rich aryl rings, which can provide for the adhesive properties.

Figure 18C:
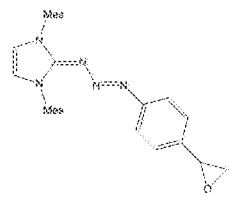
FIG. 18C shows an example of an alternative epoxide triazabutadiene.
Figure 18D:
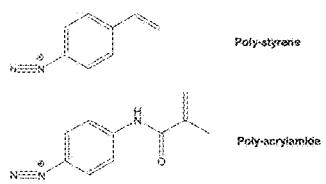
FIG. 18D shows polystyrene (as if attached to the $N_3$ area of a triazabutadiene, e.g., in lieu of an epoxide as shown in Compound 1 of FIG. 18A) and polyacrylamide (as if attached to the $N_3$ area of a triazabutadiene, e.g., in lieu of an epoxide as shown in Compound 1 of FIG. 18A). Other classes of polymers may be contemplated in lieu of epoxide, polyacrylamide, polystyrene, etc.

The present invention is not limited to triazabutadienes comprising an epoxide. For example, in some embodiments, the triazabutadiene any appropriate class of polymer (e.g., for polymerization processes), e.g., polystyrene, $\alpha$-$\beta$-unsaturated ester acrylate, or the like. The class of polymer may be one that does not require heat for polymerization (or does not require heat such that the triazabutadiene functionalities would be compromised or destroyed). For reference, FIG. 18D shows polystyrene as if attached to the $N_3$ area of a triazabutadiene, e.g., in lieu of an epoxide as shown in Compound 1 of FIG. 18A. FIG. 18D also shows polyacrylamide as if attached to the $N_3$ area of a triazabutadiene, e.g., in lieu of an epoxide as shown in Compound 1 of FIG. 18A. In some embodiments, the triazabutadiene comprises an amine. In some embodiments, the triazabutadiene has a structure similar to that of FIG. 18C, wherein the triazabutadiene is shortened relative to Compound 1 of FIG. 18A (the epoxide is directly linked to the aryl ring). In some embodiments, the triazabutadiene is an azide-containing compound that can be clicked onto other compounds as desired.

The formulation may comprise any appropriate percentage of triazabutadiene. For example, the formulation may comprise a particular percentage of triazabutadiene that provides desired properties (e.g., cure time, cure strength, color, melting/decomposition temperature, ability to heal (e.g., allow for initially unreacted triazabutadiene molecules to yield the diazonium species which subsequently bond to nearby phenol-containing compounds) of the adhesive or polymer.

In some embodiments, the formulation comprises from 0.01% to 0.1% triazabutadiene. In some embodiments, the formulation comprises from 0.01% to 1% triazabutadiene. In some embodiments, the formulation comprises from 0.01% to 10% triazabutadiene. In some embodiments, the formulation comprises from 0.01% to 20% triazabutadiene. In some embodiments, the formulation comprises from 0.1% to 1% triazabutadiene. In some embodiments, the formulation comprises from 0.1% to 10% triazabutadiene. In some embodiments, the formulation comprises from 0.1% to 20% triazabutadiene. In some embodiments, the formulation comprises from 0.1% to 30% triazabutadiene. In some embodiments, the formulation comprises from 0.1% to 40% triazabutadiene. In some embodiments, the formulation comprises from 0.1% to 50% triazabutadiene. In some embodiments, the formulation comprises from 1% to 10% triazabutadiene. In some embodiments, the formulation comprises from 1% to 20% triazabutadiene. In some embodiments, the formulation comprises from 1% to 30% triazabutadiene. In some embodiments, the formulation comprises from 1% to 40% triazabutadiene. In some embodiments, the formulation comprises from 1% to 50% triazabutadiene. In some embodiments, the formulation comprises from 1% to 60% triazabutadiene. In some embodiments, the formulation comprises from 1% to 70% triazabutadiene. In some embodiments, the formulation comprises from 1% to 80% triazabutadiene. In some embodiments, the formulation comprises from 1% to 90% triazabutadiene. In some embodiments, the formulation comprises between 10% to 20% triazabutadiene. In some embodiments, the formulation comprises between 20% to 30% triazabutadiene. In some embodiments, the formulation comprises between 30% to 40% triazabutadiene. In some embodiments, the formulation comprises between 40% to more than 50% triazabutadiene.

In some embodiments, the formulation comprises about 0.01% triazabutadiene. In some embodiments, the formulation comprises about 0.1% triazabutadiene. In some embodiments, the formulation comprises about 0.5% triazabutadiene. In some embodiments, the formulation comprises about 1% triazabutadiene. In some embodiments, the formulation comprises about 2% triazabutadiene. In some embodiments, the formulation comprises about 5% triazabutadiene. In some embodiments, the formulation comprises about 10% triazabutadiene. In some embodiments, the formulation comprises about 15% triazabutadiene. In some embodiments, the formulation comprises about 20% triazabutadiene. In some embodiments, the formulation comprises about 25% triazabutadiene. In some embodiments, the formulation comprises about 30% triazabutadiene. In some embodiments, the formulation comprises about 40% triazabutadiene. In some embodiments, the formulation comprises about 50% triazabutadiene. In some embodiments, the formulation comprises more than about 50% triazabutadiene. The present invention is not limited to the aforementioned percentages.

In some embodiments, the reaction of the triazabutadiene molecule to the diazonium species occurs in water within 10 seconds. In some embodiments, the reaction of the triazabutadiene molecule to the diazonium species occurs in water within 30 seconds. In some embodiments, the reaction of the triazabutadiene molecule to the diazonium species occurs in water within 1 minute. In some embodiments, the reaction of the triazabutadiene molecule to the diazonium species occurs in water within 5 minutes. In some embodiments, the reaction of the triazabutadiene molecule to the diazonium species occurs in water within 10 minutes. In some embodiments, the reaction of the triazabutadiene molecule to the diazonium species occurs in water within 15 minutes. In some embodiments, the reaction of the triazabutadiene molecule to the diazonium species occurs in water within 20 minutes. In some embodiments, the reaction of the triazabutadiene molecule to the diazonium species occurs in water within 25 minutes. In some embodiments, the reaction of the triazabutadiene molecule to the diazonium species occurs in water within 30 minutes. In some embodiments, the reaction of the triazabutadiene molecule to the diazonium species occurs in water within 45 minutes. In some embodiments, the reaction of the triazabutadiene molecule to the diazonium species occurs in water within 60 minutes.

In some embodiments, the bonding of the diazonium species to the phenol-containing compound occurs within 10 seconds. In some embodiments, the bonding of the diazonium species to the phenol-containing compound occurs within 30 seconds. In some embodiments, the bonding of the diazonium species to the phenol-containing compound occurs within 1 minute. In some embodiments, the bonding of the diazonium species to the phenol-containing compound occurs within 5 minutes. In some embodiments, the bonding of the diazonium species to the phenol-containing compound occurs within 10 minutes. In some embodiments, the bonding of the diazonium species to the phenol-containing compound occurs within 15 minutes. In some embodiments, the bonding of the diazonium species to the phenol-containing compound occurs within 20 minutes. In some embodiments, the bonding of the diazonium species to the phenol-containing compound occurs within 25 minutes. In some embodiments, the bonding of the diazonium species to the phenol-containing compound occurs within 30 minutes. In some embodiments, the bonding of the diazonium species to the phenol-containing compound occurs within 45 minutes. In some embodiments, the bonding of the diazonium species to the phenol-containing compound occurs within 60 minutes.

In some embodiments, light can be used to speed up the reaction. In some embodiments, varying triazabutadienes amounts can be added to speed up or slow down the reaction. In some embodiments, a surplus of triazabutadienes may be used, which may help allow for an amount of triazabutadiene molecules that are unreacted (and those unreacted triazabutadienes may be buried amongst other reacted compounds). These unreacted triazabutadienes that are buried may be useful in the event of a break in the seal. For example, a break in the seal may cause water to then react with the unreacted triazabutadiene molecules to yield the diazonium species, and those newly formed diazonium species can then subsequently bond to nearby phenol-containing compounds to perhaps "heal" the break in the seal or strengthen the bond.

The present invention also features systems (or kits) comprising said formulations, e.g., kits comprising a triazabutadiene (e.g., triazabutadiene comprising an epoxide) and an epoxy resin. In some embodiments, the kit further comprises a co-reactant (or a formulation with a co-reactant and an electron-rich aryl ring compound), wherein the formulation is adapted to react with the co-reactant to form an adhesive.

Figure 18B:
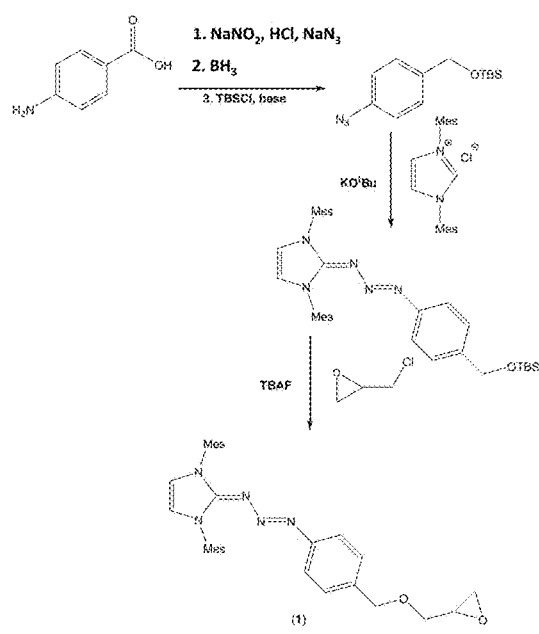
FIG. 18B shows an example of synthesis of a triazabutadiene (Compound 1) comprising an epoxide.

Triazabutadienes for use as additives to adhesive or polymerization systems may be synthesized in a variety of ways. FIG. 18B shows a non-limiting example of synthesis of a triazabutadiene (Compound 1 from FIG. 18A) comprising an epoxide. For example, in some embodiments, aryl azides that are appropriately functionalized (e.g., with an epoxide or functional group that can be converted to an alkyl azide) may be coupled with N-heterocyclic carbenes to form the triazabutadiene core. The present invention is not limited to the compound or step shown in FIG. 18B. For example, in some embodiments, TBS-Cl (tert-butyldimethylsilyl chloride) may be optional. In some embodiments, an alternative to epoxide is added to the triazabutadiene in lieu of epoxide.

As previously discussed, the covalent bond formed between the phenol-containing compound and the diazonium compound forms a colored compound. In some embodiments, the color is red, orange, or a mix of red and orange. In some embodiments, the formation of the color can be used as a positive indicator that the bonding reaction has occurred.

As previously discussed, the diazonium species, if not reacted with the phenol-containing compound, can break down into a phenolic compound (e.g., the diazonium species will extrude nitrogen gas to generate an aryl cation that will rapidly be quenched by solvating water, thus generating the phenolic compound).

This reaction is typically much slower than the second reaction (wherein the diazonium species reacts with the phenol-containing compound bound to the second surface). This phenomenon can allow for the unreacted diazonium species to eventually become non-sticky, or unreactive, which may be beneficial in certain circumstances (e.g., photolithography).

Thus, without wishing to limit the present invention to any theory or mechanism, it is believed that the system and methods of the present invention are advantageous because the technology provides underwater adhesion, the adhesive bond may be colored (e.g., highly colored azobenzene linkages), which may serve as a positive indicator that the desired reaction has occurred; and/or the chemical compounds (e.g., unreacted diazonium species) may degrade over time so that the unbonded surface does not remain sticky (e.g., adapted for adhesion) permanently.

In some embodiments, triazabutadienes of the present invention are used as after-market adhesives, e.g., formulations for application to any appropriate surface. For example, the triazabutadienes may be coated on one side of a surface and then activated (e.g., with water) to activate adhesive properties.

In some embodiments, the triazabutadienes are used as or are used in combination with bio-adhesives (e.g., natural underwater adhesives such as mussel adhesive proteins).

As previously discussed, the present invention features triazabutadienes that can cross-react with existing chemistries, e.g., epoxy chemistry), e.g., an epoxide-containing compound, an amine containing compound, an azide-containing compound that can be clicked onto other compounds as required. As an example of synthesis, aryl azides that have been appropriately functionalized (e.g., with an epoxide or functional group that can be converted to an alkyl azide) may be coupled with N-heterocyclic carbenes to form the triazabutadiene core. The present invention is not limited to this route.

As previously discussed, the properties of the formulations featuring the triazabutadiene compounds (e.g., triazabutadiene compounds with the epoxy resins or the like) may be assessed. For example, in some embodiments, gel time/cure time is assessed (e.g., assessing if it is longer, shorter, or similar as compared to samples prepared in the absence of the triazabutadiene additive). In some embodiments, cure strength is assessed (e.g., via break-strength). For example, small (e.g., 0.5×2×5 cm) molded ingots may be broken; strength may be compared to samples prepared in the absence of the triazabutadiene additive. In some embodiments, the color of the material (e.g., the final material) is assessed, e.g., color changes may be observed. In some embodiments, odor is assessed (e.g., is there a strong odor, is there a change in odor). In some embodiments, viscosity is assessed, e.g., as compared to samples prepared in the absence of the triazabutadiene additive. In some embodiments, melting/decomposition temperature is assessed, e.g., via testing in a melt-temp apparatus. In some embodiments, healing potential is assessed, e.g., ability to enhance adhesive bonding (if broken) using water. For example, in some embodiments, ingots may be cracked and submerged into water (and broken faces pushed together) and then be subjected to break-strength test.

As previously discussed, the present invention features formulations comprising a triazabutadiene molecule and an epoxide resin. In some embodiments, the epoxide resin comprises an aliphatic epoxide, e.g., a molecule according to compound B in FIG. 18A. In some embodiments, n=1-10. In some embodiments, n=1, 2, 3, 4, 5, 6, 7, 8, 9, or 10. In some embodiments, n=greater than 10. In some embodiments, the epoxide resin comprises an electron rich aryl compound, e.g., a molecule according to Compound 2 of FIG. 18A. The present invention also features methods of producing adhesives. In some embodiments, the method comprises providing a composition A, e.g., Compound 1 of FIG. 18A and Compound B of FIG. 18A; or Compound 1 of FIG. 18A and Compound B of FIG. 18A and Compound 2 of FIG. 18A. The method may further comprise providing a composition B, e.g., Compound A of FIG. 18A; or Compound A of FIG. 18A and Compound 2b of FIG. 18A. In some embodiments, m=1-5. In some embodiments, m=1, 2, 3, 4, or 5. In some embodiments, m is greater than 5. The method may further comprise mixing composition A and composition B to form a product C, product C being the adhesives. In some embodiments, product C comprises Compound 3 of FIG. 18A.

Product C above is a non-limiting example of a product of Composition A and Composition B. Product C is not limited to this structure. For example, in some embodiments, the epoxy is directly linked to the aryl ring. Note that the triazabutadiene can be attached to either the amine or epoxy side. In some embodiments, an amine is present on the triazabutadiene (in which case it could be added into the epoxy-containing monomers). In some embodiments, the method further comprises exposing product C to water, whereby a diazonium species is formed from the triazabutadiene; the diazonium species can react with an electron rich aryl compound (e.g., a phenol compound).

The present invention also features cross-linkers that respond to environmental triggers. This may allow for a chemical snapshot of a key moment of an interaction.

Example 1—Synthesis of a Fluorescent Triazabutadiene Probe

Example 1 describes transformation of a triazabutadiene into a fluorescent probe. The present invention is not limited to the compositions and methods described herein.

Figure 19:
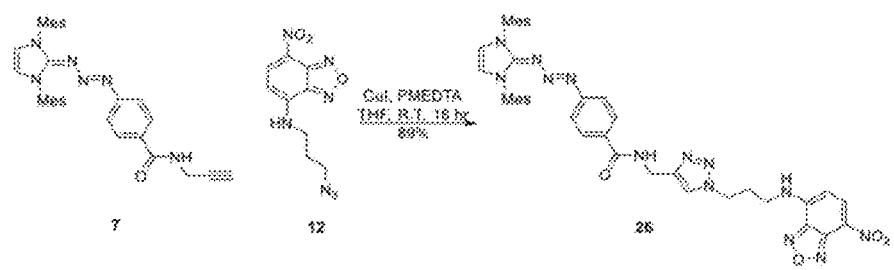
FIG. 19 shows synthesis of a fluorescent triazabutadiene.

Referring to FIG. 19, the fluorescent azide Compound 12 was coupled to the scaffold Compound 7. The yield of triazabutadiene Compound 26 was excellent. This modification added a component to the triazabutadiene by rendering the diazonium portion (upon appropriate cleavage of the triazabutadiene Compound 26) a fluorescent probe.

Example 2—Enhanced Functionalities of Triazabutadiene

Example 2 describes synthesis of a water-soluble triazabutadiene via click chemistry, a bi-functional triazabutadiene, and a triazabutadiene comprising an epoxide used to produce an alkyne handle. The present invention is not limited to the compositions and methods described herein.

Figure 20A:
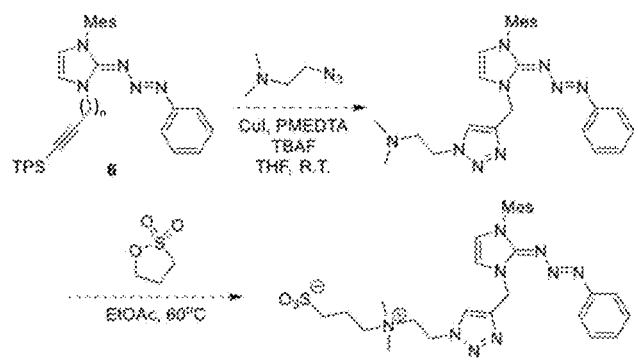
FIG. 20A shows synthesis of a water-soluble triazabutadiene via click chemistry. Note in some embodiments, n=1, n=2, n=3, n=4, etc.

Referring to FIG. 20A, in some embodiments, triazabutadienes may be made water soluble by attaching a water solubilizing agent or functional group to the triazabutadiene via click chemistry as described herein. For example, FIG. 20A shows formation of a triazole with a tertiary amine handle can undergo a nucleophilic attack on 1,3-propane sultone to synthesize a water-soluble zwitterionic triazabutadiene.

Figure 20B:
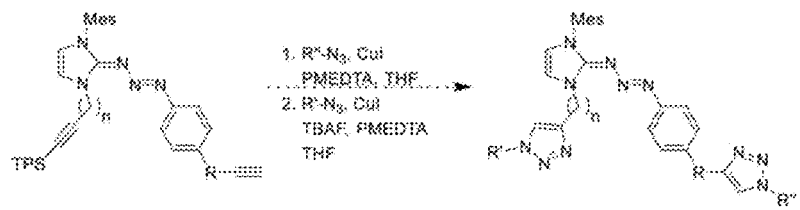
FIG. 20B shows a synthetic scheme of a bis-triazole-triazabutadiene. Note in some embodiments, n=1, n=2, n=3, n=4, etc.
Figure 21:
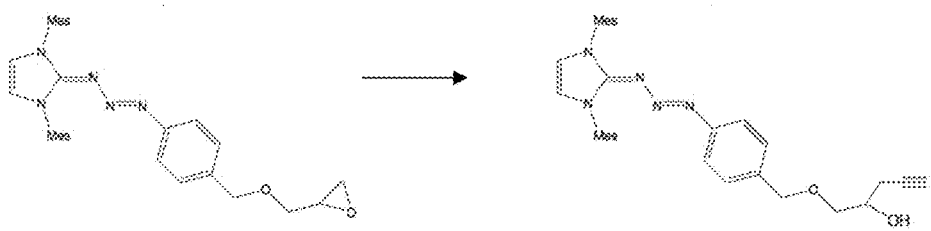
FIG. 21 shows a triazabutadiene comprising an epoxide (left) used to produce a triazabutadiene with an alkyne group adapted for click chemistry.

FIG. 20B shows a bis-alkynyl triazabutadiene comprising two alkyne handles, one on the imidazole portion and one on the aryl portion (left side). The right side of the figure shows the two alkyne handles clicked via click chemistry with an azide group. A two-handled triazabutadiene can help enhance functionality of the triazabutadiene. For example, the two handles can be used to attach two different components (e.g., biological components, e.g., a protein, a drug, etc.). For example, in some embodiments, one side is used for a first biological component and the other side is used for a second biological component. In some embodiments, one side is used for a biological component and the other side is used for a water-solubilizing component. The present invention is not limited to the aforementioned attachment components or uses for a two-handled triazabutadiene. In some embodiments, if one alkyne is protected, the other side could be preferentially used for clicking. FIG. 21 shows a triazabutadiene comprising an epoxide (left) used to produce a triazabutadiene with an alkyne group adapted for click chemistry.

The disclosures of the following documents are incorporated in their entirety by reference herein: U.S. Pat. No. 8,617,827; U.S. Pat. Application No. 2009/0048222; U.S. Pat. No. 3,591,575. U.S. Pat. No. 3,607,542; U.S. Pat. No. 4,107,353; WO Pat. No. 2008090554; U.S. Pat. No. 4,218,279; U.S. Pat. App. No. 2009/0286308; U.S. Pat. No. 4,356,050; U.S. Pat. No. 8,603,451; U.S. Pat. No. 5,856,373; U.S. Pat. No. 4,602,073; U.S. Pat. No. 3,959,210. The disclosures of the following publications are incorporated in their entirety by reference herein: Kimani and Jewett, 2015, Angewandte Chemie International Edition (DOI: 10.1002/anie.201411277—Online ahead of print). Zhong et al., 2014, Nature Nanotechnology 9, 858-866; Stewart et al., 2011, J Polym Sci B Polym Phys 49(11):757-771; Poulsen et al., 2014, Biofouling 30(4):513-23; Stewart, 2011, Appl Microbiol Biotechnol 89(1):27-33; Stewart et al., 2011, Adv Colloid Interface Sci 167(1-2):85-93; Hennebert et al., 2015, Interface Focus 5(1):2014.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A clickable triazabutadiene according to Formula C wherein both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; wherein the alkyne handle of $X^1$ is adapted to cross-link to an azide handle of a first linking component via click chemistry, and the alkyne handle of $X^2$ is adapted to cross-link to an azide handle of a second component via click chemistry, wherein the first linking component comprises a biological component and the second linking component comprises a functional group conferring water-solubility

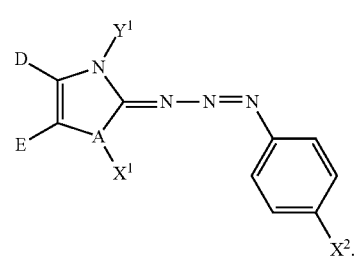

Formula C

2. The clickable triazabutadiene of claim 1, wherein the tri-substituted aryl group of $Y^1$ comprises mesityl, a NHS-ester moiety, an oligonucleotide, a peptide; a fluorescence quencher; a pro-fluorophore; an alkyne; a triazene; an aldehyde; an amine; an aminooxy; a halogen; or a combination thereof.

3. The clickable triazabutadiene of claim 1, wherein the biological component comprises a peptide, an oligonucleotide, or a drug.

4. A clickable triazabutadiene according to Formula C wherein both $X^1$ and $X^2$ comprise a terminal alkyne handle; wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and wherein $Y^1$ comprises a tri-substituted aryl group; wherein the alkyne handle of $X^1$ is adapted to cross-link to an azide handle of a first linking component via click chemistry, and the alkyne handle of $X^2$ is adapted to cross-link to an azide handle of a second component via click chemistry, wherein both the first linking component and the second linking component comprise a biological component

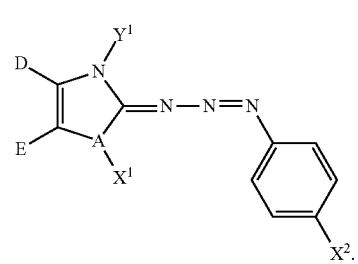

Formula C

5. The clickable triazabutadiene of claim 4, wherein the tri-substituted aryl group of $Y^1$ comprises mesityl, a NHS-ester moiety, an oligonucleotide, a peptide; a fluorescence quencher; a pro-fluorophore; an alkyne; a triazene; an aldehyde; an amine; an aminooxy; a halogen; or a combination thereof.

6. The clickable triazabutadiene of claim 4, wherein the biological component comprises a peptide, an oligonucleotide, or a drug.

7. A clickable triazabutadiene according to Formula C wherein both $X^1$ and $X^2$ comprise a terminal alkyne handle, wherein the alkyne handle of $X^1$ is adapted to cross-link to an azide handle of a first linking component via click chemistry, and the alkyne handle of $X^2$ is adapted to cross-link to an azide handle of a second component via click chemistry

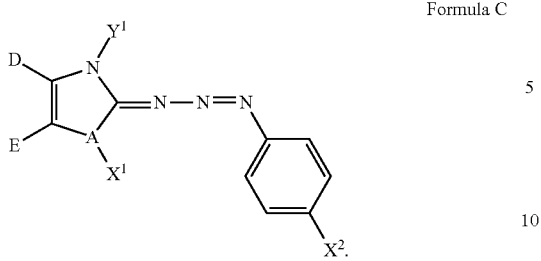

Formula C

8. The clickable triazabutadiene of claim 7, wherein A=S, O, or N; D=H, —CH=CH—CH=E-, halides, cyano, sulfonates, alkyl chain, or trifluoromethyl; E=H, —CH=CH—CH=D-, halides, cyano, sulfonates, alkyl chain, or trifluoromethyl; and $Y^1$ comprises a tri-substituted aryl group.

9. The clickable triazabutadiene of claim 8, wherein the tri-substituted aryl group of $Y^1$ comprises mesityl, a NHS-ester moiety, an oligonucleotide, a peptide; a fluorescence quencher; a pro-fluorophore; an alkyne; a triazene; an aldehyde; an amine; an aminooxy; a halogen; or a combination thereof.

10. The clickable triazabutadiene of claim 7, wherein the first linking component comprises a biological component and the second linking component comprises a functional group conferring water-solubility.

11. The clickable triazabutadiene of claim 10, wherein the biological component comprises a peptide, an oligonucleotide, or a drug.

* * * * *